United States Patent
Nolan et al.

(10) Patent No.: US 6,727,350 B2
(45) Date of Patent: Apr. 27, 2004

(54) TOSO

(75) Inventors: Garry P. Nolan, Palo Alto, CA (US); Yasumichi Hitoshi, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/135,238

(22) Filed: Aug. 17, 1998

(65) Prior Publication Data

US 2002/0177565 A1 Nov. 28, 2002

Related U.S. Application Data

(60) Provisional application No. 60/066,063, filed on Nov. 17, 1997.

(51) Int. Cl.$^7$ .............................................. C07K 16/00
(52) U.S. Cl. ................................ 530/387.9; 530/388.23
(58) Field of Search ........................... 530/387.1, 387.9, 530/388.23; 536/23.1, 23.5; 514/44, 2; 435/320.1, 325; 424/130.1

(56) References Cited

U.S. PATENT DOCUMENTS 6,114,515 A    9/2000  Wu et al.

FOREIGN PATENT DOCUMENTS

EP    0 905 238 A2    3/1999
WO    99/25832       5/1999

OTHER PUBLICATIONS

Clark TM et al. Pathology Oncology Research 5:3–15, 1999.*
Anderson WF. Nature 392 (SUPP): 25–30, 1998.*
Verma IM and Somia N. Nature 389: 239–242. 1997.*
Orkin SH and Motulsky AG, Report and Recommendations of the Panel to Assess the NIH investment in reserch on gene therapy, 1995.*
Russell et al. Principles of antibody therapy. British Medical Journal. 305:424–429, 1992.*
Mehrene t al. Monoclonal anti–body based therapy. Current Opinion in Oncology. 8:493–498, 1996.*
Itoh, et al., "The Polypeptide Encoded by the cDNA for human Cell Surface Antigen Fas Can Mediate Apoptosis," *Cell*, 66:233–243 (1991).
Yonehara, et al., "A Cell–Killing Monoclonal Antibody (ANTI–Fas) to a Cell Surface Antigen Co–Downregulated with the Receptor of Tumor Necrosis Factor," *J. Exp. Med.*, 169:1747–1756 (1989).
Itoh and Nagata, "A Novel Protein Domain Required for Apoptosis," *J. Biol. Chem.*, 268:10932–10937 (1993).
Boldin, et al.,. "A Novel Protein that Interacts with the Death Domain of Fas/APO1 Contains a Sequence Motif Related to the Death Domain," *J. Biol. Chem.*, 270:7795–7798 (1995).

Chinnaiyan, et al., "FADD, a Novel Death Domain–Containing Protein, Interacts with the Death Domain of Fas and Initiates Apoptosis," *Cell*, 8145:505–512 (1995).
Chu, et al., "A Fas–associated Protein Factor, FAF1, Potentiates Fas–mediated Apoptosis," *Proc. Natl. Acad. Sci. USA*, 92:11894–11898 (1995).
Okura, et al., "Protection Against Fas/APO–1– and Tumor Necrosis Factor–Mediated Cell Death by a Novel Protein, Sentrin," *J. Immunol.*, 157:4277–4281 (1996).
Sato, et al., "FAP–1: A Protein Tyrosine Phosphatase that Associates with Fas," *Science*, 268:411–415 (1995).
Stanger, et al., "RIP: A Novel Protein Containing a Death Domain that Interacts with Fas/APO–1 (CD95) in Yeast and Causes Cell Death," *Cell*, 8145:513–523 (1995).
Enari, et al., "Involvement of an ICE–like Protease in Fas–Mediated Apoptosis," *Nature*, 375:78–81 (1995).
Enari, et al., "Sequential Activation of ICE–like and CPP32–like Protease During Fas–Mediated Apoptosis," *Nature*, 380:723–726 (1996).
Tewari et al., "Fas– and Tumor Necros is Factor–Induced Apoptosis Inhibited by the Poxvirus crmA Gene Product," *J. Biol. Chem*, 270:3255–3260 (1995).
Fernandes–Alnemri, et al., "In Vitro Activation of CPP32 and Mch3 by Mch4, a Novel Human Apoptotic Cysteine Protease Containing Two FADD–Like Domains," *Proc. Natl. Acad Sci. USA*, 93:7464–7469 (1996).
Muzio, et al., "FLICE, A Novel FADD–Homologous ICE/CED–3–like Protease, is Recruited to the CD95 (Fas/APO–1) Death–Inducing Signaling Complex," *Cell*, 85:817–827 (1996).
Irmler, et al., "Inhibition of Death Receptor Signals by Cellular FLIP,"60 *Nature*, 388:190–195 (1997).
Srinivasula, et al., "FLAME–1, a Novel FADD–like Anti–Apoptotic Molecule that Regulates Fas/TNFR1–induced Apoptosis," *J. Biol. Chem.*, 272:18542–18545 (1997).
Hu, et al., "I–FLICE, a Novel Inhibitor of Tumor Necrosis Factor Receptor–1– and CD–95–Induced Apoptosis," *J. Biol. Chem.*, 272:17255–17257 (1997).
Cifone, et al., "Apoptotic Signaling Through CD95 (Fas/Apo–1) Activates an Acidic Sphingomyelinase," *J. Exp. Med.*, 180:1547–1552 (1994).

(List continued on next page.)

*Primary Examiner*—Ram R. Shukla
(74) *Attorney, Agent, or Firm*—James S. Keddie; Bozicevic, Field & Francis LLP

(57) ABSTRACT

The present invention is directed to novel polypeptides such as the the Toso protein and related molecuels which have an inhibitory effect on TNF mediated apoptosis and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

3 Claims, 11 Drawing Sheets

OTHER PUBLICATIONS

Tian, et al., "Fas–Activated Scrine/Threonine Kinase (FAST) phosphorylate TII During Fas–Mediated Apoptosis," *J. Exp. Med.*, 182:865–874 (1995).

Yang, et al., "Daxx, A Novel Fas–Binding Protein that Activates JNK and Apoptosis," *Cell*, 89:1067–1076 (1997).

Richardson, et al., "Fas Ligation Tiggers Apoptosis in Macrophages but not Endothelial Cells," *Eur. J. Immunol.*, 24:2640–2645 (1994).

Arase, et al., "Fas–Mediated Cytotoxicity by Freshly Isolated Natural Killer Cells," *J. Exp. Med.*, 181:1235–1238 (1995).

Berke, "The CTL's Kiss of Death," *Cell*, 81:9–12 (1995).

Montel, et al., "Fas Involvement in Cytotoxicity mediated by Human NK Cells,"*Cell Immunol.*, 166:236–246 (1995).

Klas, et al., "Activation Interferes with the APO–1 Pathway in Mature Human T Cells," Int. Immunol., 5(6):625–630 (1993).

Owen–Schaub, et al., "DNA Fragmentation and Dell Death is Selectively Triggered in Activated Human Lymphocytes by Fas Antigen Engagement," *Cell Immunol.*, 140:197–205 (1992).

Los et al., "Requirement of an ICE/CED–3 Protease for Fas/APO–1–Mediated Apoptosis," *Nature*375:81–83 (1995).

Hitoshi et al., "Toso, a Cell Surface, Specific Regulator of Fas–Induced Apoptosis in T Cells," *Immunity*, 8:461–471(Apr. 1998).

Rothenberg et al., "Intracellular Combinatorial Chemistry with Peptides in Selection of Caspase–like Inhibtiors," *NATO ASI Series, Gene Therapy* ,H(105)171–183 (1998).

* cited by examiner aaaggagtaagcagcgtgtctccatcccctctctagggggctcttgg ATGGACCTTGCACTCTAGAAGGGACAATGGACT
TCTGGCTTTGGCCACTTTACTTCCTGCCAGTATCAGGGGCCCTG AGGATCCTCCCAGAAGTAAAGGTAGAGGGGAGCTG
GGCGGATCAGTTACCATCAAATGCCCACTTCCTGAAATGCATGTGAGGATATATCTGTGCCGGGAGATGGCTGGATCTGG
AACATGTGGTACCGTGGTATCCACCACCAACTTCATCAAGGCAGAATACAAGGGCCGAGTTACTCTGAAGCAATACCCAC
GCAAGAATCTGTTCCTAGTGGAGGTAACACAGCTGACAGAAAGTGACAGCGGAGTCTATGCCTGCGGAGCGGGCATGAAC
ACAGACCGGGAAAGACCCAGAAAGTCACCCTGAATGTCCACAGTGAATACGAGCCATCATGGGAAGAGCAGCCAATGCC
TGAGACTCCAAAATGGTTTCATCTGCCCTATTTGTTCCAGATGCCTGCATATGCCAGTTCTTCCAAATTCGTAACCAGAG
TTACCACACCAGCTCAAAGGGGCAAGGTCCCTCCAGTTCACCACTCCTCCCCCACCACCCAAATCACCCACCGCCCTCGA
GTGTCCAGAGCATCTTCAGTAGCAGGTGACAAGCCCCGAACCTTCCTGCCATCCACTACAGCCTCAAAAATCTCAGCTCT
GGAGGGGCTGCTCAAGCCCCAGACGCCCAGCTACAACCACCACACCAGGCTGCACAGGCAGAGAGCACTGGACTATGGCT
CACAGTCTGGGAGGGAAGGCCAAGGA TTTCACATCCTGATCCCGACCATCCTGGGCCTTTTCCTGCTGGCACTTCTGGGG
CTGGTGGTGAAAAGGGCCGTTGAAAGGAGG AAAGCCCTCTCCAGGCGGGCCCGCCGACTGGCCGTGAGGATGCGCGCCCT
GGAGAGCTCCCAGAGGCCCCGCGGGTCGCCGCGACCGCGCTCCCAAAACAACATCTACAGCGCCTGCCCGCGGCGCGCTC
CTGGAGCGGACGCTGCAGGCACAGGGGAGGCCCCCGTTCCCGGCCCCGGAGCGCCGTTGCCCCCCGCCCCGCTGCAGGTG
TCTGAATCTCCCTGGCTCCATGCCCCATCTCTGAAGACCAGCTGTGAATACGTGAGCCTCTACCACCAGCCTGCCGCCAT
GATGGAGGACAGTGATTCAGATGACTACATCAATGTTCCTGCCTGA caactcccagctatccccaacccaggctcgg
actgtggtgccaaggagtctcatctatctgctgatgtccaatacctgcttcatgtgttctcagagccctcatcacttccc
atgccccatctcgactcccatcccatctatctgtgccctgagcatggctctgcccccaggtcgtcttgcacaccttggc
agcccctgtagttgacaggtaagctgtaggcatgtagagcaattgtcccaatgccacttgcttcctttccaagccgtcg
aacagactgtgggatttgcagagtgtttcttccatgtctttgaccacagggttgttgctgcccaggctctagatcacatg
gcatcaggctggggcagaggcatagctattgtctcgggcatccttccaggggttgggtcttacacaaatagaaggctctt
gctctgagttatgtgacgtgcctcagccccatggactaagcaggggtctggtataaaaacactcctggaaacgcctttgc
cctgatccaaatgttagcacttgctagtgaacgtctacttatctcaagttctatgctaaaggcaatttatcttgatgtga
tgataaaccaaacttattagcaagatatgcatatatatccataaattctctttactctgtctccatcctttt Coding region: Capitalized
    Leader sequence: Underlined
    Transmembrane region: Double underlined

Figure 1

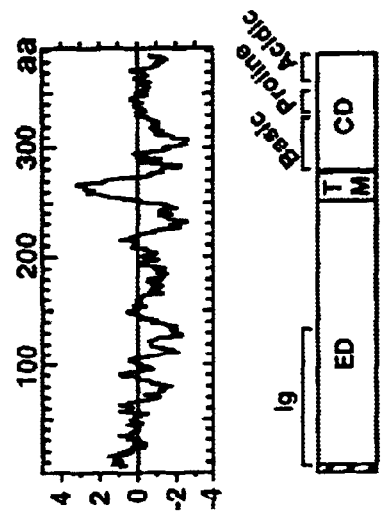

```
a)
  1  MDEMLNPLYT LPVSGALRIL PEVKVEGELG GSVTIKCPLP EMHVRIYLCR
 51  ENAGSGTCGT VVSTTNFIKA EYKGRVTLKQ YPRKNLFLVE VTQLTESDSG
101  VYACGAGMNT DRGKTQKVTL NVHSEYEPSW EEQPMPETPK WFHLPYLFQM
151  PAYASSSKFV TRVTTPAQRG KVPPVHHSSP SRASSVAGDK
201  PKTFLPSTTA SKIESALEGLL KPQTPSYNHH TRLHRQRALD YGSQSGREGQ
251  GFHLIIPTIL GLFLAALGL  VYKRAVERRK ALSRRARRLA VRMRALESSQ
301  RPRGSPRPRS QNNIYSACPR RARGADAAGT GEAPVPGPGA PLPPAPLQVS
351  ESPWLHAPSL KTSCEYVSLY HQPAAMMEDS DSDDYINVPA
```

Figure 2

TOSO

This is a continuing application of U.S. S.No. 60/066,063, filed Nov. 17, 1997.

FIELD OF THE INVENTION

The invention relates to novel Toso proteins, nucleic acids and antibodies. The invention further relates to the use of bioactive agents such as Toso proteins, nucleic acids and antibodies capable of modulating Fas or tumor necrosis factor ("TNF") receptor mediated apoptosis for the diagnosis and treatment of disease.

BACKGROUND OF THE INVENTION

Apoptosis or programmed cell death is an important homeostatic mechanism that maintains cell number, positioning, and differentiation. Several intracellular and intercellular processes are known to regulate apoptosis. One of the best characterized systems is initiated by the cell surface receptor, Fas (Apo-1/CD95), homologues of which initiate apoptosis in a wide range of organisms (Itoh, et al., Cell, 66:233–243 (1991); Yonehara, et al, J. Exp. Med., 169:1747–1756 (1989)). Clustering of the Fas cytoplasmic domain generates an apoptotic signal via the "death domain" (Itoh and Nagata, J. Biol. Chem., 268:10932–10937 (1993)). Several critical proteins that bind to the death domain or other domains within the cytoplasmic region have been identified using yeast two-hybrid and biochemical screens (Boldin, et al., J. Biol. Chem., 270:7795–7798 (1995); Chinnaiyan, et al., Cell, 8145:505–512 (1995); Chu, et al., Proc. Natl. Acad. Sci. USA, 92:11894–11898 (1995); Okura, et al, J. Immnunol., 157:4277–4281 (1996); Sato, et al., Science, 268:411–415 (1995); Stanger, et al., Cell, 8145:513–523 (1995)).

Fas engagement by Fas ligand is capable of activating the interleukin-1β converting enzyme family of cysteine proteases (Caspases)—the proteolytic executors of apoptosis (Enari, et al., Nature, 375:78–81 (1995); Enari, et al., Nature, 380:723–726 (1996); Los, et al., Nature, 375:81–83 (1995); Tewari and Dixit, J. Biol. Chem, 270:3255–3260 (1995)). Recent studies implicate caspase8 (MACH/FLICE/Mch5) as linking Fas receptor signaling to downstream caspases via its association with FADD/MORT1 (Boldin, et al., (1995); Chinnaiyan, et al., (1995); Boldin, et al., (1996); Fernandes-Alnemri, et al., Proc. Natl. Acad Sci. USA, 93:7464–7469 (1996); Muzio, et al., Cell, 85:817–827 (1996)). Several groups have reported that caspase-8 activation is inhibited by a cellular inhibitor, cFLIP/FLAME-1/I-FLICE (Irmler, et al., Nature, 388:190–195 (1997); Srinivasula, et al., J. Biol. Chem., 272:18542–18545 (1997); Hu, et al., J. Biol. Chem., 272:17255–17257 (1997)). Other proteins involved in Fas-mediated apoptosis include: (a) the Fas-activated serine/threonine kinase (FAST kinase), which is rapidly activated during Fas-mediated apoptosis; (b) acid sphingomyelinase, which produces ceramide, a pro-apoptotic signal that acts as a second messenger in several systems; and (c) Daxx, a novel protein that links Fas to the JNK stress kinase pathway (Cifone, et al., J. Exp. Med., 180:1547–1552 (1994); Tian, et al., J. Exp. Med., 182:865–874 (1995); Yang, et al., Cell, 89:1067–1076 (1997)). The exact role of these latter co-activators has yet to be fully defined.

A balance between life and programmed cell death signals in cells is likely to be governed by multiple interacting regulators that counteract apoptotic signals with appropriate anti-apoptotic signals. Imbalances in this regulation can result in wide variety of pathologies, including cancer and immune dysfunction and it is now clear that other polypeptides besides Fas contribute to disregulation of appropriately induced apoptosis. As an example, in many tumor cell lines Fas expression does not correlate with sensitivity to Fas-induced apoptosis, implying the existence of Fas-resistance protein (Richardson, et al., Eur. J. Immunol., 24:2640–2645 (1994)). Also, in some types of cells, Fas-induced apoptosis requires protein synthesis inhibitors such as cycloheximide (Itoh and Nagata, (1993); Yonehara, et al., (1989)) and even in Fas-sensitive cells, protein synthesis inhibitors can play a synergistic role with cycloheximide (Itoh and Nagata, (1993)). These combined observations further suggest the existence of proteins capable of suppressing Fas-generated apoptotic signaling.

Additionally, in the course of a normal immune response, both cytotoxic T cell and NK cell activation can lead to Fas ligand (FasL) induction of apoptosis in target cells (Arase, et al., J. Exp. Med., 181:1235–1238 (1995); Berke, Cell, 81:9–12 (1995); Montel, et al., Cell Immunol., 166:236–246 (1995)). Although both Fas and FasL are rapidly induced following T-cell activation, activated-T cells remain resistant to Fas-induced apoptosis for several days (Klas, et al., Int. Immunol., 5:625–630 (1993); Owen-Schaub, et al., Cell Immunol., 140:197–205 (1992)). Thus, a mechanism exists to shield newly activated T cells from the cytotoxicity of their own FasL expression. This is likely to be an important component of T cell activation processes and protection in lymph nodes, splenic germinal centers and other sites at which T cell activation results in apoptosis of target cells.

Described herein is the identification and characterization of a novel surface molecule, "Toso" which is a member of the immunoglobulin gene superfamily and which specifically inhibits Fas and TNF receptor family mediated apoptosis. The results demonstrate the existence of cell surface mediated signaling pathways that lead to down regulation of Fas-mediated apoptosis in certain cell types and suggest that activation of T cells suppresses internal signaling systems that might lead inappropriately to T cell-induced self-killing.

Accordingly, it is an object of the invention to provide Toso proteins and related molecules. It is a further object of the invention to provide recombinant nucleic acids encoding Toso proteins, and expression vectors and host cells containing the nucleic acid encoding the Toso protein. A further object of the invention is to provide methods for screening for antagonists and agonists of Toso.

SUMMARY OF THE INVENTION

In accordance with the objects outlined above, the present invention provides recombinant nucleic acids encoding a Toso protein that will hybridize under high stringency conditions to the nucleic acid sequence depicted in FIG. 1 (SEQ ID NO:1) or its complement. Recombinant nucleic acids encoding Toso proteins that are at least about 70% identical to the amino acid sequence depicted in FIG. 1 (SEQ ID NO:1) are also provided, as well as recombinant nucleic acid that is at least about 70% identical to the nucleic acid sequence depicted in FIG. 1 (SEQ ID NO:1) or its complement.

In a further aspect, the invention provides expression vectors and host cells comprising the nucleic acids of the invention, and processes for producing a Toso protein comprising culturing the host cells under conditions suitable for expression of a Toso protein.

In an additional aspect, the invention provides Toso proteins, and antibodies that bind to Toso proteins.

Further provided are methods of modulating apoptosis in a cell comprising administering to the cell a recombinant nucleic acid encoding a Toso protein, and methods for treating an apoptosis related condition in a mammal comprising administering a recombinant nucleic acid encoding a Toso protein.

BRIEF DESCRIPTION OF THE DRAWINGS

FIG. 1 depicts the nucleotide sequence (SEQ ID:NO 1) of Toso. Also presented are the positions of the initiator ATG start codon, the stop codon the nucleotides which correspond to the signal sequence and the nucleotides which correspond to the putative transmembrane domain of the Toso protein.

FIG. 2a depicts the amino acid sequence (SEQ ID:NO 2) of amino acids 1 to 390 deduced from nucleotides 1 to 1173 of the nucleotide sequence shown in FIG. 1 (SEQ ID:NO 1). Two hydrophobic regions are underlined.

FIG. 2b depicts a Kyte-Dolittle hydropathy plot analysis of Toso gene product (upper) and schematic presentation of Toso (bottom). The mature Toso is a 390-amino acid protein with the leader sequence of 17 amino acids (hatched bar), the extracellular domain of 236 amino acids (ED), the transmembrane region of 20 amino acids (TM; dotted bar) and the cytoplasmic domain of 117 amino acids (CD). The immunoglobulin domain (Ig), the basic amino acid-rich region (Basic), the proline-rich region (Proline), and the acidic amino acid-rich region (Acidic) are indicated.

The hemagglutinin (HA) tag is indicated as a light shaded bar. The percentage of apoptotic cells is expressed as the mean (hatched and shaded bar)±SD of triplicate cultures.

Figure 6:
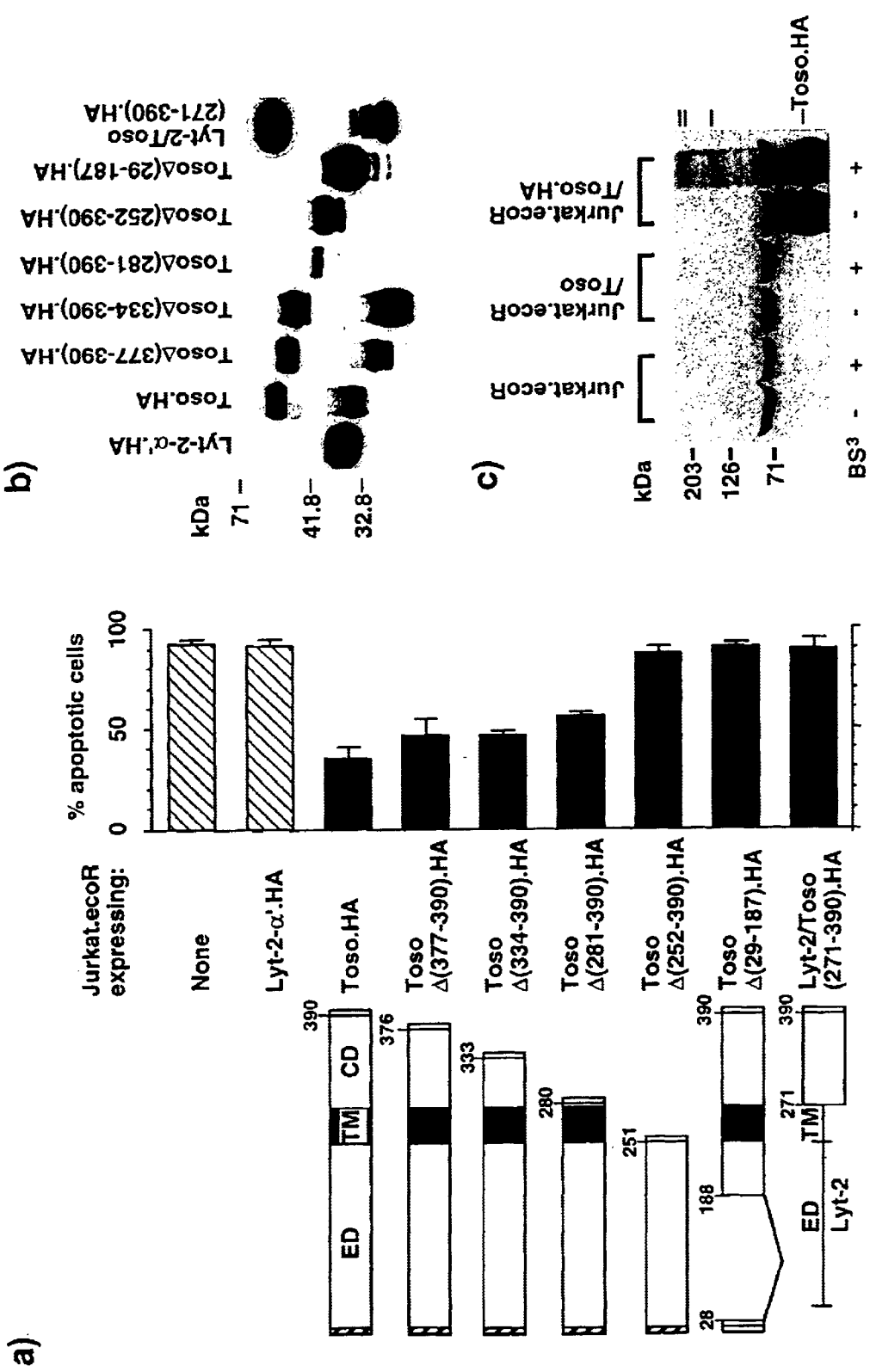
FIG. 6a depicts the effect of Toso deletion mutant expression on anti-Fas mAb-induced apoptosis. Structure of the Toso deletion mutants is shown at the left side of this panel. Full-length Toso is a 390-amino acid protein with the leader sequence of 17 amino acids (hatched bar), the extracellular domain of 236 amino acids (ED), the transmembrane region of 20 amino acids (TM; dark-shaded bar) and the cytoplasmic domain of 117 amino acids (CD).

FIG. 6b depicts Western blot analysis of deletion mutants using anti-HA antibody. The molecular weight of major products from Toso.HA, TosoΔ(377–390).HA, TosoΔ (334–390). HA, Toso Δ (252–390). HA, TosoΔ (281–390). HA, TosoΔ (29 187). HA and Lyt-2/Toso(271–390).HA was 60/35, 55/30, 50/26, 40, 38, 35, 60/30 kDa, respectively. Positions and sizes (kDa) of standard protein markers are indicated in left side of panel FIG. 6c depicts Crosslinking the extracellular domain of Toso. Positions of standard protein markers and Toso.HA are indicated in left side and right of panel, respectively.

Figure 7:
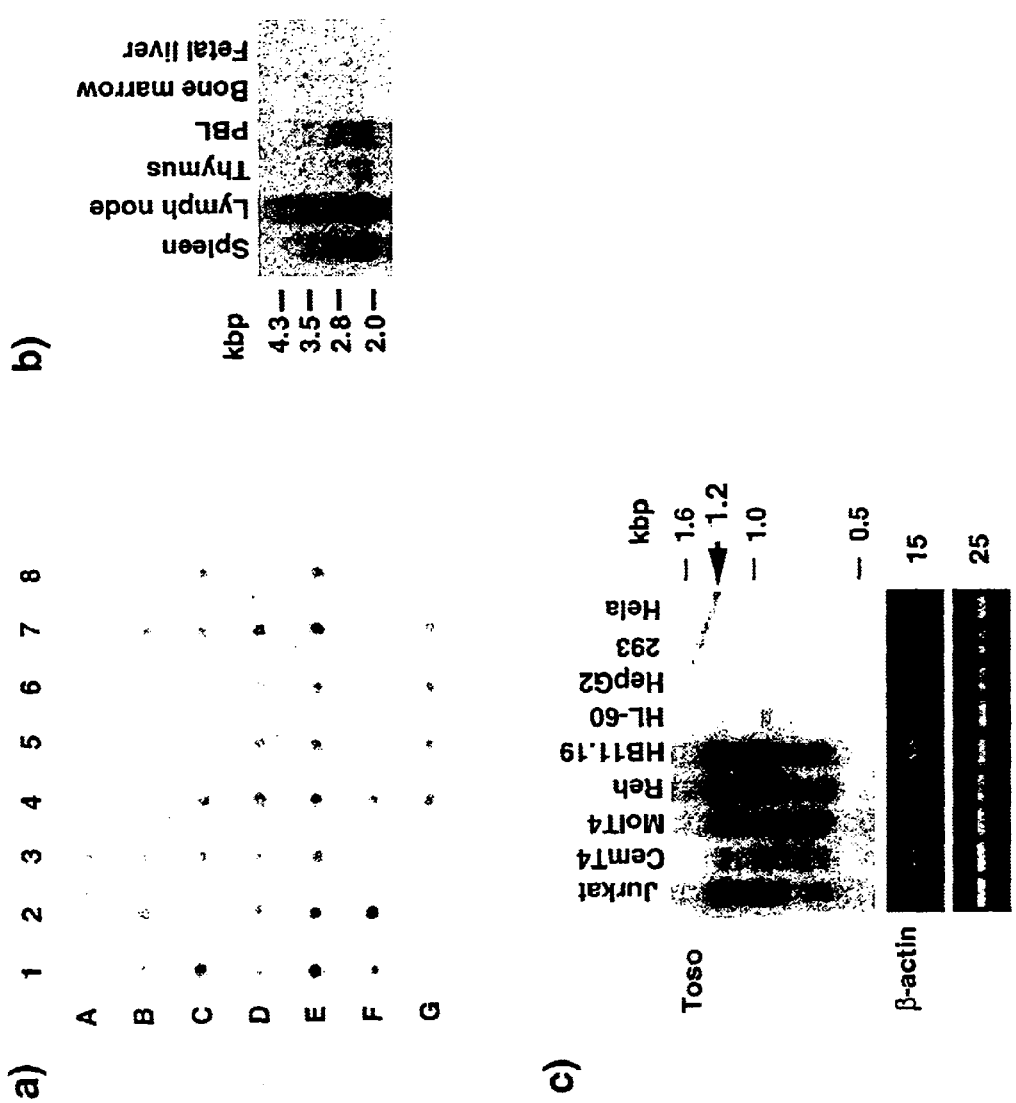

FIG. 7a depicts mRNA dot blot analysis of Toso gene in several human tissues.

FIG. 7b depicts Northern blot analysis of Toso gene in several human immune tissues. Positions and sizes (kbp) of Toso mRNA are indicated in left side of panels.

FIG. 7c depicts RT-PCR analysis of Toso in human cell lines (upper panel). Positions and sizes (kbp) of Toso and standard nucleotide makers are indicated. As a control for loading, we amplified β-actin cDNA (lower panels).

Figure 8:
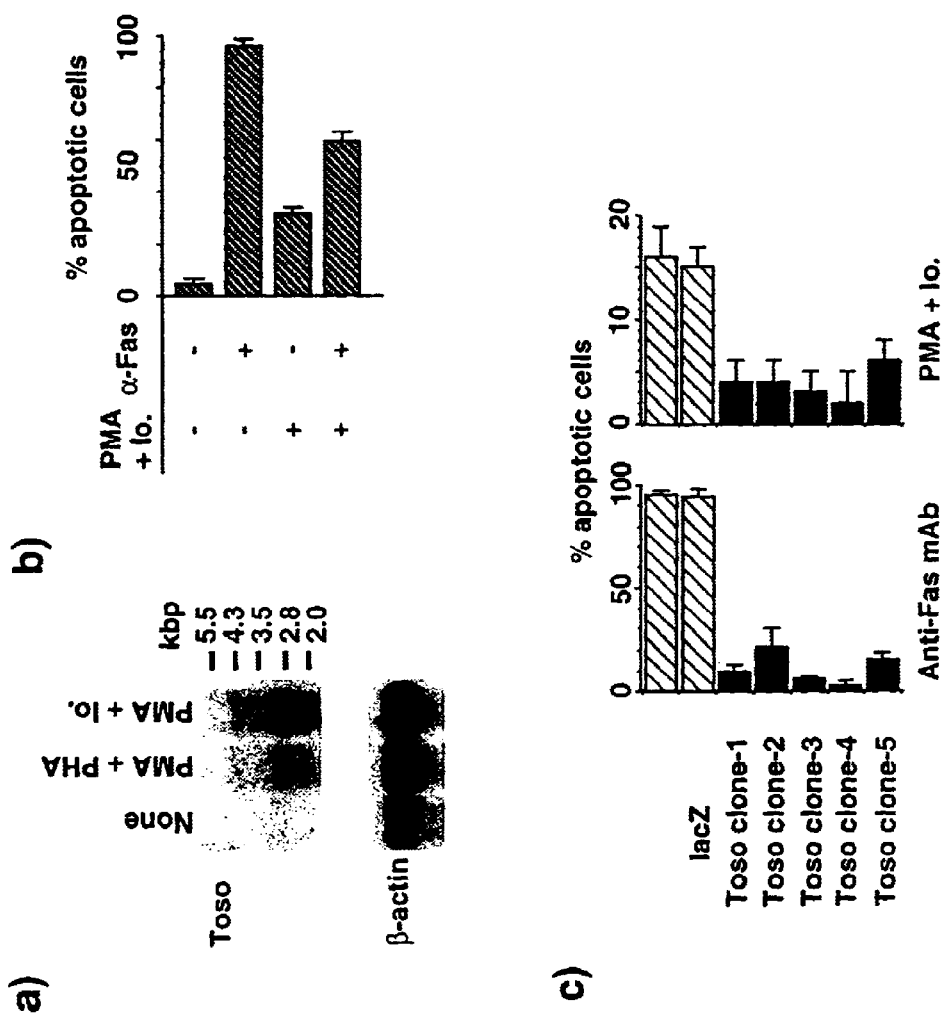

FIG. 8a depicts (a) Northern blot analysis of Toso gene in Jurkat cells (None) and Jurkat cells stimulated with PMA and PHA (PMA+PHA) or PMA and lonomycin (PMA+lo.). RNA was electrophoresed, transferred to a Hybond N+ membrane and hybridized with a radiolabelled probe specific for Toso (upper) and β-actin (lower). Film was exposed at −70° C. with an intensifying screen for two days (upper). Positions and sizes (kbp) of Toso mRNA are indicated in right side of panels.

FIG. 8b depicts activation induced resistance to anti-Fas mAb-induced apoptosis in Jurkat cells. The percentage of apoptotic cells are expressed as the mean (hatched bar)±SD of triplicate cultures.

FIG. 8c depicts the effect of Toso on PMA and lonomycin (PMA+lo.)-induced apoptosis. Jurkat.ecoR cells (−), Jurkat.ecoR cells infected with pBabeMN-lacZ (lacZ), pBabeMN-Toso-infected clones (Toso clones 1–5) were cultured with 10 ng/ml of anti-Fas mAb (left), 10 ng/ml PMA and 500 ng/ml Ionomycin (right) for 24 hours. The percentage of apoptotic cells are expressed as the mean (hatched bar and shaded bar)±SD of triplicate cultures.

Figure 9:
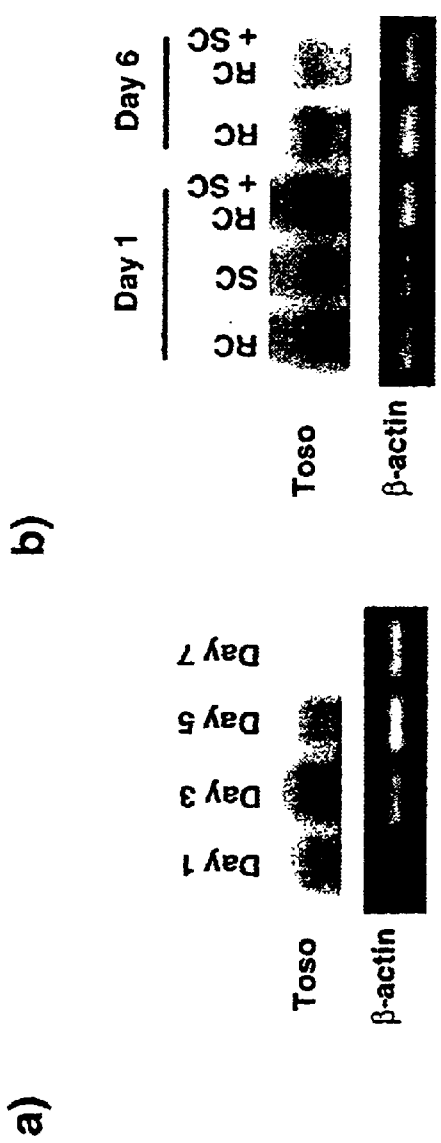

FIG. 9a depicts the RT-PCR analysis of Toso in peripheral blood mononuclear cells after activation with PHA (upper panel, the 1.2 kbp fragment of Toso).

FIG. 9b depicts analysis of Toso in peripheral blood mononuclear cells after allogenic stimulation (upper panel, the 1.2 kbp fragment of Toso). Stimulator cells (SC), responder cells (RC) or mixed cells (RC+SC) were cultured for one day (day 1) and six days (day 6).

Figure 10:
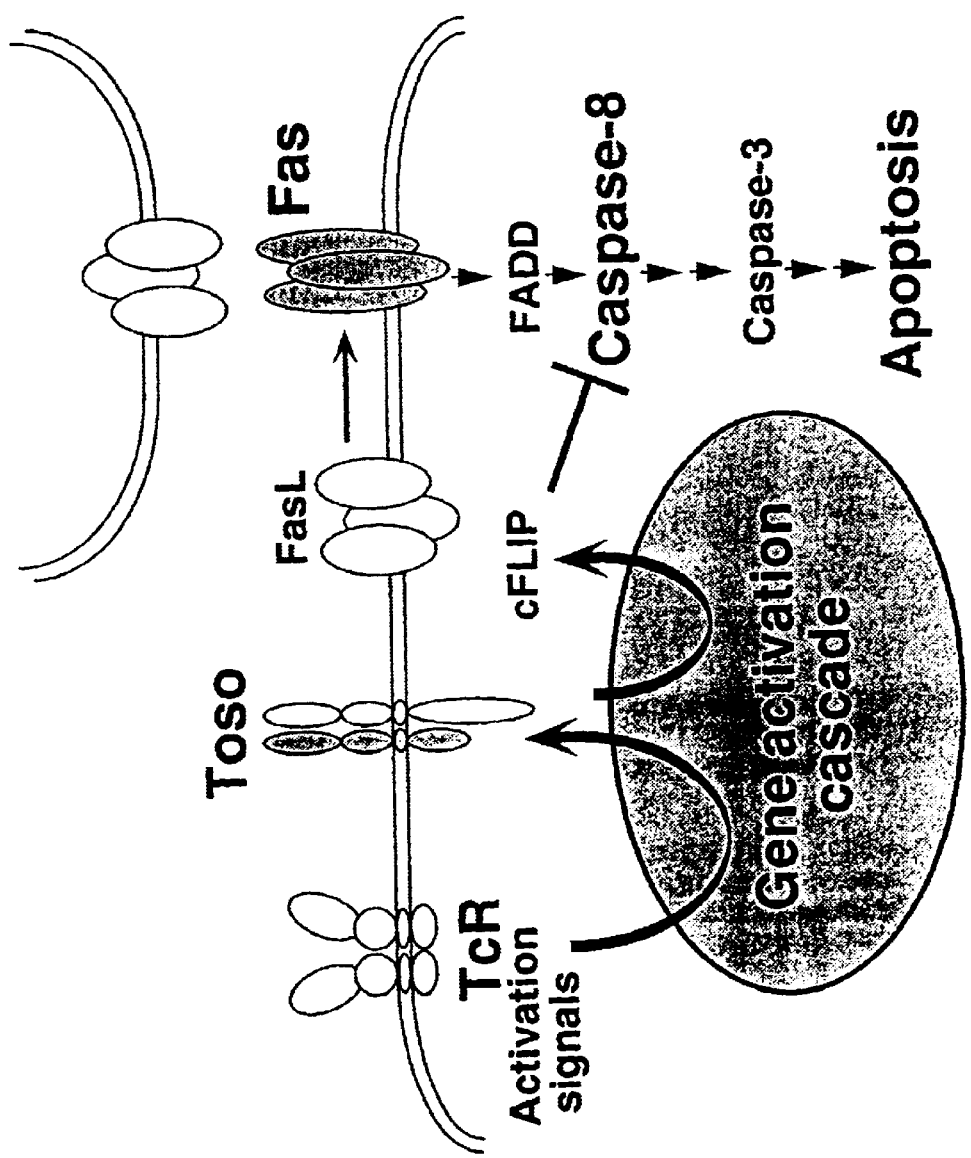

FIG. 10 depicts a model for the role of Toso in T cell activation. In the model, the role of Toso is to be induced following T cell activation and to protect T cells from self-induced programmed cell death. The inhibitory effects of Toso on Fas signaling maps at the level of caspase-8 through induced expression of cFLIP.

Figure 11:
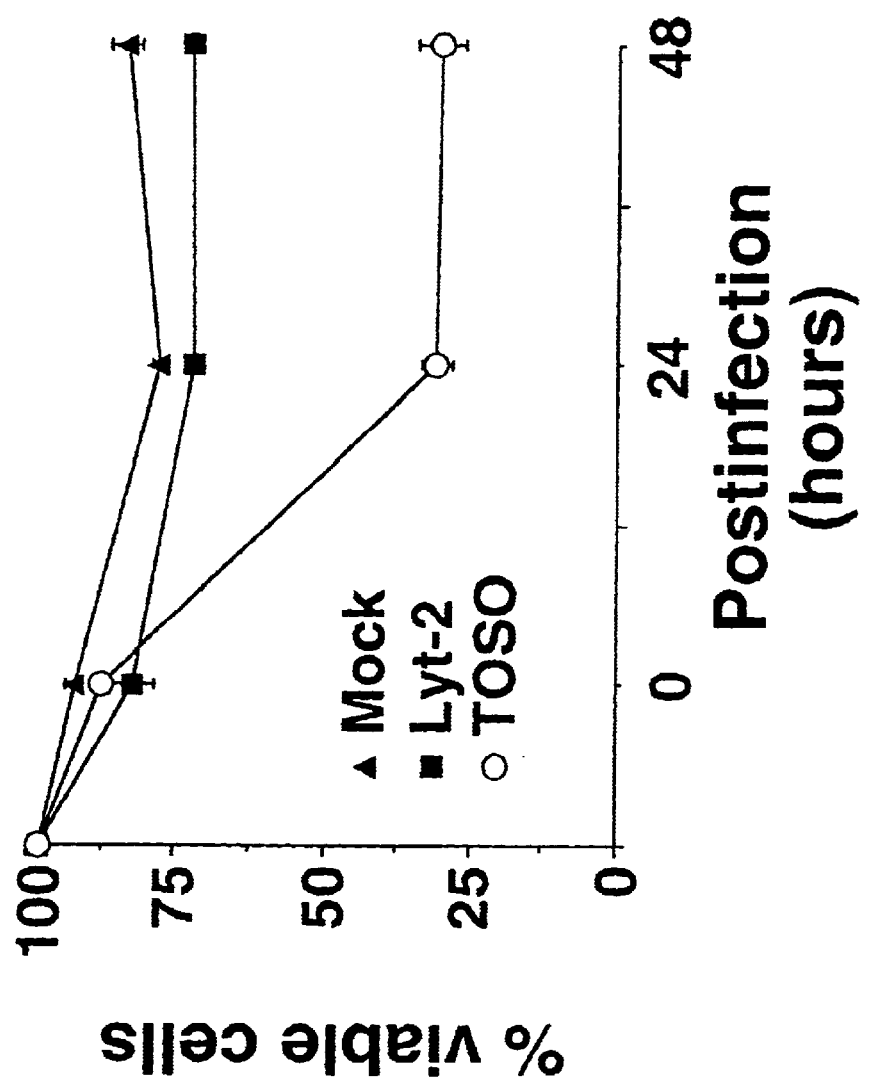

FIG. 11 depicts massive cell death of 70 Z3 cells induced by TOSO. 70Z/3 cells were incubated with supernatant from ϕNX-E (closed triangle), viral supernatant of pBabeMN-Lyt-2O (closed square), or pBabeMN-TOSO (open circle) for 12 hours including the initial spinning at 2500 rpm for 90 min. Infection frequency of pBabeMN-Lyt-2O was determined to be 79% at 48 hours post infection. The percentage of viable cells at various time points are expressed as mean (symbol)±SD (vertical bar) of triplicate cultures.

DETAILED DESCRIPTION OF THE INVENTION

The present invention provides novel Ig domain-containing Toso polypeptides, with potent pathway-specific anti-apoptotic effects in hematopoietic cells. Toso (named after a Japanese liquor that is drunk on New Year's Day to celebrate long life and eternal youth) exerts an inhibitory activity against apoptosis induced by Fas-, TNF-α-, FADD and PMA/Ionomycin but not against staurosporine- or ceramide-induced apoptosis. Without being bound by theory, the mechanism of blocking apoptotic activation, and the pathway specificity of the effect, is most likely explained by Toso induction of cFLIP expression which inhibits caspase-8 processing. Toso is expressed within lymphoid tissues and hematopoietic cells, and is enhanced after T-cell activation, which suggests an important role for this and related molecules in the immune system.

Accordingly, the present invention provides Toso proteins and nucleic acids. In a preferred embodiment, the Toso proteins are from vertebrates and more preferably from mammals including dogs, cats and rabbits, rodents (including rats, mice, hamsters, guinea pigs, etc.), primates (including chimpanzees, African green monkeys, etc.), farm animals (including sheep, goats, pigs, cows, horses, etc.) and in the most preferred embodiment, from humans. However, using the techniques outlined below, Toso proteins from other organisms may also be obtained.

As outlined herein, the Toso proteins of the present invention are IgG superfamily molecules which are expressed in a variety of tissue types, including, but not limited to lymph nodes, peripheral blood leukocytes, thymus, lung, and kidney. As further outlined herein, Toso proteins exert pathway specific anti-apoptotic effects in hematopoietic cells. Toso is a membrane bound protein, as it contains a putative transmembrane domain. The extracellular domain of Toso has homology to immunoglobulin variable domains.

A Toso protein of the present invention may be identified in several ways. "Protein" in this sense includes proteins, polypeptides, and peptides. A Toso nucleic acid or Toso protein is initially identified by substantial nucleic acid and/or amino acid sequence homology to the sequences shown in FIGS. 1 and 2a. Such homology can be based upon the overall nucleic acid or amino acid sequence.

As used herein, a protein is a "Toso protein" if the overall homology of the protein sequence to the amino acid sequence shown in FIG. 2a (SEQ ID NO:2) is preferably greater than about 50 or 60%, more preferably greater than about 70 or 75%, even more preferably greater than about 80% and most preferably greater than 85%. In some embodiments the homology will be as high as about 90 to 95 or 98%. Homology in this context means sequence similarity or identity, with identity being preferred. Identical in this context means identical amino acids at corresponding positions in the two sequences which are being compared. Homology in this context includes amino acids which are identical and those which are similar (functionally equivalent). This homology will be determined using standard techniques known in the art, such as the Best Fit sequence program described by Devereux, et al., *Nucl. Acid Res.*, 12:387–395 (1984), preferably using the default settings, or the BLASTX program (Altschul, et al., *J. Mol. Biol.*, 215:403–410 (1990)). The alignment may include the introduction of gaps in the sequences to be aligned. In addition, for sequences which contain either more or fewer amino acids than the proteins shown in the Figures, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

As outlined herein, Toso proteins have several important domains. Toso contains a cytoplasmic domain from amino acids 273 to 390, with the extracellular domain spanning from 18 to 253 (unless otherwise specified, all amino acid numbering is based on the human sequence). Toso contains a standard transmembrane domain, spanning from amino acids 254 to 272. Toso contains an additional hydrophobic region at the N-terminus, amino acids 1 to 17, corresponding to a putative signal sequence. In addition, the cytoplasmic domain of Toso contains a basic amino acid-rich region (from Arg274 to Arg323), a proline rich region (from Pro334 to P346), and an acidic amino acid-rich region (from Glu378 to Asp384). In addition, the cytoplasmic domain has partial homology to FAST kinase, acid sphingomyleinase, insulin receptor substrate-1 (IRS-1) and the apoptosis inhibitor from *Orgyia pseudotsugata* nuclear polyhedrosis virus (Op-1AP ). The extracellular domain of Toso has homology to the immunoglobulin V-region.

As used herein, a protein is also a "Toso protein" if the homology of the cytoplasmic domain comprising amino acids 273 to 390, or the extracellular domain comprising amino acids 18 to 253, respectively, of the amino acid sequence shown in FIG. 2a (SEQ ID NO:2) is preferably greater than about 50% of 60%, more preferably greater than about 70% or 75%, even more preferably greater than about 80% and most preferably greater than 85%. In some embodiments the homology will be as high as about 90 to 95 or 98%.

Toso proteins of the present invention may be shorter or longer than the amino acid sequences shown in the Figures. Thus, in a preferred embodiment, included within the definition of Toso proteins are portions or fragments of the sequences depicted in the Figures. As outlined herein, Toso deletion mutants can be made, including, but not limited to, the deletion of amino acids 377–390, 334–390, 281–390, 252–390, and 29–187. As further outlined herein, Toso fusion proteins can be made including, but not limited to, the fusion of amino acids 1–271. A preferred Toso fragment is the cytoplasmic domain of Toso, which may modulate apoptosis, as shown herein. A further preferred Toso fragment is the extracellular domain of Toso, comprising roughly the first 236 amino acids of Toso, which is required for the anti-apoptotic effects on Fas antibody-stimulated cells. However, as outlined herein, preferred fragments of Toso also include a transmembrane domain, as it may be involved in signaling and Fas-induced apoptosis by Toso may require its insertion into membranes.

Thus, in a preferred embodiment, the Toso proteins of the present invention are Toso polypeptides. In this embodiment, a Toso polypeptide comprises at least the immunoglobin V-like domain, and preferably a transmembrane domain, although it may contain additional amino acids as well. As shown in the Examples and discussed below, Toso is an IgG superfamily protein which is capable of inhibiting apoptosis mediated by members of the Fas or TNF receptor family of proteins.

In a preferred embodiment, the Toso proteins are derivative or variant Toso proteins. That is, as outlined more fully below, the derivative Toso peptide will contain at least one amino acid substitution, deletion or insertion, with amino acid substitutions being particularly preferred. The amino acid substitution, insertion or deletion may occur at any residue within the Toso peptide. As outlined below, particularly preferred substitutions are made within the extracellular domain or cytoplasmic domain of the Toso protein.

In addition, as is more fully outlined below, Toso proteins can be made that are longer than those depicted in the figures, for example, by the addition of epitope or purification tags, the addition of other fusion sequences, etc.

Toso proteins may also be identified as being encoded by Toso nucleic acids. Thus, Toso proteins are encoded by nucleic acids that will hybridize to the sequence depicted in FIG. 1, or its complement, as outlined herein.

In a preferred embodiment, when the Toso protein is to be used to generate antibodies, the Toso protein must share at least one epitope or determinant with the full length protein shown in FIG. 2a. By "epitope" or "determinant" herein is meant a portion of a protein which will generate and/or bind an antibody. Thus, in most instances, antibodies made to a smaller Toso protein will be able to bind to the fill length protein. In a preferred embodiment, the epitope is unique; that is, antibodies generated to a unique epitope show little or no cross-reactivity. In a preferred embodiment, the antibodies are generated to an extracellular portion of the Toso molecule, i.e. to all or some of the N-terminal region from amino acid numbers 18–253.

In a preferred embodiment, the antibodies to Toso are capable of reducing or eliminating the biological function of Toso, as is described below. That is, the addition of anti-Toso antibodies (either polyclonal or preferably monoclonal) to cells comprising Toso receptors may reduce or eliminate the Toso receptor activity, blocking the signaling pathway that blocks apoptosis; that is, when Toso receptor function is reduced or eliminated, the cells die. Generally, at least a 50% decrease in activity is preferred, with at least about 75% being particularly preferred and about a 95–100% decrease being especially preferred.

The Toso antibodies of the invention specifically bind to Toso proteins. By "specifically bind" herein is meant that the antibodies bind to the protein with a binding constant in the range of at least $10^6$–$10^8$ M, with a preferred range being $10^7$–$10^9$ M.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 1 is preferably greater than 50 or 60%, more preferably greater than about 70 to 75%, particularly greater than about 80% and most preferably greater than 85%. In some embodiments the homology will be as high as about 90 to 95 or 98%.

In a preferred embodiment, a Toso nucleic acid encodes a Toso protein. As will be appreciated by those in the art, due to the degeneracy of the genetic code, an extremely large number of nucleic acids may be made, all of which encode the Toso proteins of the present invention. Thus, having identified a particular amino acid sequence, those skilled in the art could make any number of different nucleic acids, by simply modifying the sequence of one or more codons in a way which does not change the amino acid sequence of the Toso.

In one embodiment, the nucleic acid homology is determined through hybridization studies. Thus, for example, nucleic acids which hybridize under high stringency to the nucleic acid sequences shown in FIG. 1 or its complement is considered a Toso gene. High stringency conditions are known in the art; see for example Maniatis, et al., *Molecular Cloning: A Laboratory Manual,* 2d Edition (1989), and Short Protocols in Molecular Biology, ed. Ausubel, et al., both of which are hereby incorporated by reference. [An example of such conditions includes hybridization at about 65° C. in about 5×SSPE and washing conditions of about 65° C. in about 0.1× SSPE.

In another embodiment, less stringent hybridization conditions are used; for example, moderate or low stringency conditions may be used, as are known in the art; see Maniatis and Ausubel, supra. An example of such conditions includes hybridization at about 50 to 55° C. in 5×SSPE and washing conditions of about 50° C. in about 5×SSPE.

The Toso proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated Toso nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations;

however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a Toso protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Once identified, the polypeptides comprising the biologically active sequences may be prepared in accordance with conventional techniques, such as synthesis (for example, use of a Beckman Model 990 peptide synthesizer or other commercial synthesizer).

Also included within the definition of Toso proteins of the present invention are amino acid sequence variants. These variants fall into one or more of three classes: substitutional, insertional or deletional variants. These variants ordinarily are prepared by site specific mutagenesis of nucleotides in the DNA encoding the Toso protein, using cassette or PCR mutagenesis or other techniques well known in the art, to produce DNA encoding the variant, and thereafter expressing the DNA in recombinant cell culture as outlined above. However, variant Toso protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the Toso protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Toso variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Toso protein activities; for example, for binding domain mutations, competitive binding studies such as are outlined in the Examples may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. For example, a preferred variant comprises the deletion of the cytoplasmic domain, leaving only the extracellular domain of Toso, preferably including the transmembrane domain. Additional preferred variants comprise the cytoplasmic domain alone or a soluble receptor (i.e. the extracellular domain lacking the transmembrane domain).

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Toso protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the Toso proteins as needed. Alternatively, the variant may be designed such that the biological activity of the Toso protein is altered, For example, glycosylation sites, and more particularly one or more O-linked or N-linked gylcosylation sites may be altered or removed. Either or both of the transmembrane domains may be altered or removed, to make a soluble or secreted protein, i.e. the extracellular domain.

Covalent modifications of Toso polypeptides are included within the scope of this invention. One type of covalent modification includes reacting targeted amino acid residues of a Toso polypeptide with an organic derivatizing agent that is capable of reacting with selected side chains or the N-or C-terminal residues of a Toso polypeptide. Derivatization with bifunctional agents is useful, for instance, for crosslinking Toso to a water-insoluble support matrix or surface for use in the method for purifying anti-Toso antibodies or screening assays, as is more fully described below. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutarnyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins; Structure and Molecuar Properties*, W. H. Freeman & Co., San Francisco, pp. 79–86 (1983)], acetylation of the N-terminal amine, and amidation of any C-terminal carboxyl group.

Another type of covalent modification of the Toso polypeptide included within the scope of this invention comprises altering the native glycosylation pattern of the polypeptide. "Altering the native glycosylation pattern" is intended for purposes herein to mean deleting one or more carbohydrate moieties found in native sequence Toso polypeptide, and/or adding one or more glycosylation sites that are not present in the native sequence Toso polypeptide.

Addition of glycosylation sites to Toso polypeptides may be accomplished by altering the amino acid sequence thereof. The alteration may be made, for example, by the addition of, or substitution by, one or more serine or threonine residues to the native sequence Toso polypeptide (for O-linked glycosylation sites). The Toso amino acid sequence may optionally be altered through changes at the DNA level, particularly by mutating the DNA encoding the Toso polypeptide at preselected bases such that codons are generated that will translate into the desired amino acids.

Another means of increasing the number of carbohydrate moieties on the Toso polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the Toso polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo-and exo-glycosidases as described by Thotakura, et al., *Meth. Enzymol.*, 138:350 (1987).

Another type of covalent modification of Toso comprises linking the Toso polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

Toso polypeptides of the present invention may also be modified in a way to form chimeric molecules comprising a Toso polypeptide fused to another, heterologous polypeptide or amino acid sequence. In one embodiment, such a chimeric molecule comprises a fusion of a Toso polypeptide with a tag polypeptide which provides an epitope to which an anti-tag antibody can selectively bind. The epitope tag is generally placed at the amino-or carboxyl-terminus of the Toso polypeptide. The presence of such epitope-tagged forms of a Toso polypeptide can be detected using an antibody against the tag polypeptide. Also, provision of the epitope tag enables the Toso polypeptide to be readily purified by affinity purification using an anti-tag antibody or another type of affinity matrix that binds to the epitope tag. In an alternative embodiment, the chimeric molecule may comprise a fusion of a Toso polypeptide with an immunoglobulin or a particular region of an immunoglobulin. For a bivalent form of the chimeric molecule, such a fusion could be to the Fc region of an IgG molecule or GST fusions.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field, et al., *Mol. Cell Biol.*, 8:2159–2165 (1988)]; the c-myc tag and the 8F9, 3C7, 6E10, G4, B7, and 9E10 antibodies thereto [Evan, et al., *Molecular and Cellular Biology*, 5:3610–3616 (1985)]; and the Herpes Simplex virus glycoprotein D (gD) tag and its antibody [Paborsky, et al., *Protein Engineering*, 3(6):547–553 (1990)]. Other tag polypeptides include the Flag-peptide [Hopp, et al., *BioTechnology*, 6:1204–1210 (1988)]; the KT3 epitope peptide [Martin, et al., *Science*, 255:192–194 (1992)]; tubulin epitope peptide [Skinner, et al., *J. Biol. Chem.*, 266:15163–15166 (1991)]; and the T7 gene 10 protein peptide tag [Lutz-Freyermuth, et al., *Proc. Natl. Acad. Sci. USA*, 87;6393–6397 (1990)].

Also included with the definition of Toso protein are other Toso proteins of the Toso family, and Toso proteins from other organisms, which are cloned and expressed as outlined below. Thus, probe or degenerate polymerase chain reaction (PCR) primer sequences may be used to find other related Toso proteins from humans or other organisms. As will be appreciated by those in the art, particularly useful probe and/or PCR primer sequences include the unique areas of the Toso nucleic acid sequence. Thus, useful probe or primer sequences may be designed to: all or part of the sequence of the immunoglobulin V-like Toso domain, all or part of the unique extracellular domain, which spans roughly amino acids 18–253, or sequences outside the coding region. As is generally known in the art, preferred PCR primers are from about 15 to about 35 nucleotides in length, with from about 20 to about 30 being preferred, and may contain inosine as needed. The conditions for the PCR reaction are well known in the art.

Once the Toso nucleic acid is identified, it can be cloned and, if necessary, its constituent parts recombined to form the entire Toso nucleic acid. Once isolated from its natural source, e.g., contained within a plasmid or other vector or excised therefrom as a linear nucleic acid segment, the recombinant Toso nucleic acid can be further-used as a probe to identify and isolate other Toso nucleic acids. It can also be used as a "precursor" nucleic acid to make modified or variant Toso nucleic acids and proteins.

Using the nucleic acids of the present invention which encode a Toso protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Toso protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Toso protein; for example, transcriptional and tnanslational regulatory nucleic acid sequences from Bacillus are preferably used to express the Toso protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The Toso proteins of the present invention are produced by culturing a host cell transformed with an expression vector containing nucleic acid encoding a Toso protein, under the appropriate conditions to induce or cause expression of the Toso protein. The conditions appropriate for Toso protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells, for example primary cells, including stem cells, including, but not limited to bone marrow stem cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jukat cells, human cells and other primary cells.

In a preferred embodiment, the Toso proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for Toso protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, the CMV promoter, a retroviral LTR promoter, mouse maloney luekemia virus LTR, or pBabeMN.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Toso proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Toso protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the Toso protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, Toso proteins are produced in insect cells. Expression vectors for the transformation of insect cells, and in particular, baculovirus-based expression vectors, are well known in the art.

In a preferred embodiment, Toso protein is produced in yeast cells. Yeast expression systems are well known in the art, and include expression vectors for *Saccharomyces cerevisiae, Candida albicans* and *C. matiosa, Hansenula polymorpha, Kluyveromyces fragilis* and *K. lactis, Pichia guillerimondii* and *P. pastoris, Schizosaccharomyces pombe,* and *Yarrowia lipotytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The Toso protein may also be made as a fusion protein, using techniques well known in the art. Thus, for example, for the creation of monoclonal antibodies, if the desired epitope is small, the Toso protein may be fused to a carrier protein to form an immunogen. Alternatively, the Toso protein may be made as a fusion protein to increase expression, or for other reasons. For example, when the Toso protein is a Toso peptide, the nucleic acid encoding the peptide may be linked to other nucleic acid for expression purposes.

In one embodiment, the Toso nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the Toso protein is purified or isolated after expression. Toso proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Toso protein may be purified using a standard anti-Toso antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the Toso protein. In some instances no purification will be necessary.

Once expressed and purified if necessary, the Toso proteins and nucleic acids are useful in a number of applications.

In a preferred embodiment, modified Toso cell-surface receptors, and cells containing the modified receptors, are made. In one embodiment, non-human animals (preferably transgenic) are made that contain modified Toso receptors; similarly, "knock-out" animal models and Toso transgenic animals that may contain an inducible promoter may be made. In addition, cells, particularly mammalian, can be made comprising a modified Toso cell surface receptor.

In one embodiment, the Toso proteins of the present invention may be used to generate polyclonal and monoclonal antibodies to the full length protein, the extracellular or cytoplasmic domains of Toso proteins, which are useful as described herein. Similarly, the Toso proteins can be coupled, using standard technology, to affinity chromatography columns. These columns may then be used to purify Toso antibodies. In a preferred embodiment, the antibodies are generated to epitopes unique to the Toso protein; that is, the antibodies show little or no cross-reactivity to other proteins. These antibodies find use in a number of applications. For example, the Toso antibodies may be coupled to standard affinity chromatography columns and used to purify Toso proteins. The antibodies may also be used as described below.

In a preferred embodiment, antibodies, particularly monoclonal antibodies, are used to modulate the biological function of a Toso protein. "Modulating the activity of Toso" includes an increase in activity, a decrease in activity, or a change in the type or kind of activity present. By "Toso activity" or grammatical equivalents herein is meant the ability of Toso after activation to modulate apoptosis. As outlined herein, upon T cell activation, Toso is activated, initiating a signaling pathway that results in modulation of apoptosis. Such modulation may result in response to either of the extracellular or cytoplasmic domains of Toso and may correspond to a decrease or an increase in apoptosis. In a preferred embodiment, the activity of Toso (either or both of the extracellular or cytoplasmic domain of Toso) is increased; in another preferred embodiment, the activity of Toso is decreased.

In a preferred embodiment, methods of modulating apoptosis in a cell are provided, comprising administering to the cell a recombinant nucleic acid encoding a Toso protein, or a Toso protein. This includes treating an apoptosis related condition or apoptosis mediated disorders, which include, but are not limited to, any disease characterized by T cell overactivity, including, but not limited to Sjogrens mixed connective tissue disease, autoimmune disorders including, but not limited to, lupus (SLE), rheumatoid arthritis (RA), multiple sclerosis, and autoimmune diseases which are tissue specific, for example liver (hepatitis), kidney (nephritis) or Hashimoto (thyroiditis); diseases where T cells actively destroy cells, for example, cytotoxic effects including, but not limited to, transplant rejection, disease conditions based on graft vs. host or host vs. graft reactions; conditions where cells of any kind that are not dying express Toso appropriately, for example, cancer of T or B cell origin (where increased apoptosis would be desirable), including but not limited to, leukemias and lymphomas, Chrohn's disease, skin inflammatory disorders (psoriasis, eczema); and diseases secondary to altered immunoglobulin production such as Waldenstroms, and multiple myeloma.

In one embodiment, a therapeutically effective dose of a Toso is administered to a patient. This may be done either by the administration of a Toso protein, or a nucleic acid encoding a Toso protein, as is known in the art. By "therapeutically effective dose" herein is meant a dose that produces the effects for which it is administered. The exact dose will depend on the purpose of the treatment, and will be ascertainable by one skilled in the art using known techniques. As is known in the art, adjustments for Toso degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the Toso proteins of the present invention can be done in a variety of ways, including, but not limited to, orally, subcutaneously, intravenously, intranasally, transcermally, intraperitoneally, intramuscularly, intrapulmonary, vaginally, rectally, or intraocularly. In some instances, for example, in the treatment of wounds and inflammation, the Toso may be directly applied as a solution or spray.

The pharmaceutical compositions of the present invention comprise a Toso protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE I

Molecular Cloning and Chromosomal Localization of Toso

Jurkat cells (human T cell line, a gift of Dr. Calvin Kuo, Harvard Univ.) were infected with a retroviral Jurkat T cell cDNA library to screen for cDNAs that encode inhibitory molecules for Fas-induced apoptosis. A retroviral library containing $2 \times 10^6$ independent cDNA inserts was constructed from Jurkat cell mRNA by standard methods (Kinoshita and Nolan, unpublished) using a retrovirus vector pBabeMN (Kinoshita, et al. (1997)). The library was transfected into an ecotropic virus packaging cell line, φNX-Ampho, as described previously. Jurkat cells were spin-infected with the supernatant from φNX-A cells resulting in 20–40% infection using this method as determined by doping of the library with a marker retrovirus pBabeMN-LacZ or pBabeMN-Lyt-2-α (194 amino acids), which does not have cytoplasmic domain (Tagawa, et al., Proc. Natl. Acad. Sci, 83:3422–3426 (1986)). Jurkat cells were aliquoted into 96-well plates in media containing 10 ng/ml of anti-human Fas mAb, CH11, (Kamiya Biomedical Company, CA 91359, U.S.A.) for 15 days. Jurkat cells, under conditions empirically derived, were sensitive to Fas-mediated apoptosis with a spontaneous survival rate under our conditions of 2–3 per $10^6$ cells. Cells that survived the Fas-mediated killing were identified by outgrowth in the 96 well plate format, expanded, total RNA extracted, and cDNA inserts rescued using RT-PCR (AMV reverse transcriptase from Promega, Wis. 53711, U.S.A. and Vent DNA polymerase New England Biolabs, Inc., MA 01915, U.S.A.) with primers 5'-GCT CAC TTA CAG GCT CTC TA (SEQ ID NO:22) (LibS) and 5'-CAG GTG GGG TCT TTC ATT CC (SEQ ID NO:23) (LibA), which were located 282 bp and 56 bp nucleotides upstream and downstream of cDNA insert cloning sites. After an initial denaturation at 94° C. for 5 minutes, each cycle of amplification consisted of 30 second denaturation at 94° C., followed by a 30 second-annealing at 58° C. and 2 minutes extension at 72° C. After 35 cycles, the final product was extended for 10 minutes at 72° C. The rescued inserts were digested with BamHI-SalI (Promega) or BstXI (Promega), and ligated into the pBabeMN retrovirus vector. The cloned retrovirus containing the novel insert was infected into Jurkat cells. Cells were cultured with 10 ng/ml anti-Fas mAb to confirm whether the inhibitory effect was caused by cDNA inserts of retrovirus. 26 clones were obtained that were resistant to Fas-induced apoptosis, of which 12 carried cDNA inserts. After a second round of anti-Fas screening, one clone, termed here Toso, demonstrated potent inhibition of Fas-induced apoptotic signaling.

The cDNA insert of Toso was found to contain a 5'-non-coding region of 73 nucleotides, a coding region of 1173 nucleotides (390 amino acids) and a 3'-non-coding region of 665 nucleotides. (See FIG. 1, SEQ ID NO:1). The ATG initiation codon is contained within a standard Kozak consensus sequence. Kyte-Doolittle hydropathy plot analysis showed that Toso has two hydrophobic regions: the amino-terminal residues from 1 to 17 correspond to the deduced signal sequence (underlined) and residues from 254 to 272 (double underlined) correspond to a presumptive transmembrane region [Hofmann and Stoffel, f993, analysis was performed using DNAsis-Mac V2.0 (Hitachi Software Engineering, Co. Ltd., Japan)], suggesting that Toso is a type I integral membrane protein. (See FIG. 2b). The predicted molecular weight of Toso is 41 kDa. The cytoplasmic region of Toso has a basic amino acid-rich region (from $R^{274}$ to $R^{323}$), a proline-rich region (from $P^{334}$ to $P^{346}$), and an acidic amino acid-rich region (from $E^{378}$ to $D^{384}$) (See FIGS. 2a and 2b, SEQ ID NO: 2). BLAST search analysis revealed that Toso is a unique gene (Altshul, et al., (1990)). The extracellular domain of Toso has homology to the immunoglobulin variable (IgV) domains, which is characterized by motifs in the β-strand B, D and F regions, (residues VTLTC, RV(or F, 1) and DSG(or A)-Y-CA ) (Williams and Barclay, Ann. Rev. Immunol., 6:381–405 (1988)). Importantly, the cysteines in the IgV-like motif VTIKC at position 33 in Toso, as well as the cysteine in the IgV-like motif DSGVYAC at position 98, are appropriately distanced as in other IgV-like domains to form a disulphide bond. Toso also contains within the Ig domains two additional cysteines that are not conserved in other IgV-like domains. Thus, the presumptive extracellular domain has all the requisite features that demarcate it as a potential IgV-like domain. The cytoplasmic region of Toso has partial homology to FAST kinase, acid sphingomyelinase, insulin receptor substrate-1 (IRS-1) and the apoptosis inhibitor from Orgyia pseudotsugata nuclear polyhedrosis virus (Op-lAP) (FIG. 3), which might function to initiate some of the signaling systems acted upon by Toso.

The Toso gene was mapped to a human chromosome by using a panel of 17 human X Chinese hamster hybrid cell lines derived from several independent fusion experiments (Francke et al., 1986). PCR primers used to amplify Toso sequence derived from the 3' untranslated region were 5'-AGA GGC ATA GCT ATT GTC TCG G (SEQ ID NO:24) (sense; located 369 bp downstream of the coding region), and 5'-ACA TTT GGA TCA GGG CAA AG (SEQ ID NO:25) (anti-sense; 508 bp downstream of the coding region). The size of the PCR product was 159 bp. The PCR conditions were 94° C., 90 seconds; then 35 cycles of 94° C., 20 seconds; 55° C., 30 seconds; 72° C., 45 seconds; followed by 72° C., 5 minutes. Specific PCR products were obtained from human genomic DNA, and hybrid cell lines that carry human chromosome 1. The PCR product was sequenced to confirm its identity.

To map the Toso gene locus more precisely, two human radiation hybrid (RH) mapping panels were typed by PCR. GeneBridge 4 (Whitehead Institute/MIT Genome Center) and Stanford G3 (Stanford Human Genome Center), were obtained from Research Genetics, Inc. (Cox, et al., Science, 250:245–250 (1990); Walter, et al., Net Gene 7:22–28 (1994)), and samples were typed using the primers and PCR conditions described above. Results of the maximum likelihood analysis (Boehnke, et al., Am. J. Hum. Genet., 49:1174–1188 (1991)) were obtained by submitting the raw scores to: http:/www-genome.wi.mit.edu/cgibin/contig/rhmapper.pl and http://wwwshgc.stanford.edu/rhserver2/rhserver_form.html. The cytological localization of the Toso gene was deduced from the cytogenetic information about the flanking markers in Bray-Ward et al (Bray-Ward, et at., Genomics, 32:1–14 (1996)). In the Stanford G3 mapping panel, Toso cosegregated with chromosome 1 marker D1S3553 on all 83 Stanford G3 panel RH cell lines. D1 S3553 is a known marker of chromosome 1 bin 115 on the SHGC RH map. In the GeneBridge 4 mapping panel, Toso is located 5.4 $cR_{3000}$ and 1.7 $cR_{3000}$ from D1 S504 and W1-9641, respectively. The order of loci in this region from centromere to qter is: D1S412-D1S306 D1S504-Toso-W1-9641-D1S491-D1S237. According to Bray-Ward et al. (1996), the YACs containing the more proximal markers D1S412 (bin 104), D1S477 (bin 109) and D1S504 (bin 114) were mapped to 1q25-q32, 1q31-q32 and 1q25-q32 respectively, and the YACs containing the more distal markers D1 S491 (bin 118), D1 S414 (bin 121) and D1 S237 (bin 124) were mapped to essentially the same region, 1q31-q32, 1q31-q32 and 1q32-q41, respectively. Thus, the Toso gene is located at 1q31-q32, a region in which several chromosomal abnormalities relating to leukemias are localized.

Toso is a negative regulator of Fas-mediated cell death in lymphoid cells, and may therefore be involved in oncogenic events or resistance to chemotherapy (Friesen, et al., Nature Medicine, 2:574–577 (1996)). The gene for Toso localizes within human chromosome region 1q31-q32. Chromosomal changes in 1q32 are frequently observed in human cancer, including various types of hematopoietic malignancies and solid tumors (Jinnai, et al., *Am. J. Hematol*, 35:118–124 (1990); Mertens, et al., *Cancer Res.*, 57:2765–2780 (1997); Mitelman, et al., *Nat Genet.*, 417–474 (1997); Schmid and Kohler, *Cancer Genet. Cytogenet*, 11:121–23 (1984); Shah, et al., *Cancer Genet. Cytogenet*, 61:183–192 (1992); Waghray, et al., *Cancer Genet. Cytogenet*, 23:225–237 (1986); Yip, et al., *Cancer Genet. Cytogenet*, 51:235–238 (1991)). Furthermore, studies in nude mice demonstrated that duplication of the chromosome segment of 1 q11-q32 is associated with proliferation and metastasis of human chronic lymphocyte leukemic B-cells (Ghose, et al., *Cancer Res.*, 50:3737–3742 (1990)), suggesting the presence of dominantly acting growth regulatory or cell survival genes. Thus, Toso is a candidate for evaluation as a proto-oncogene in several proliferative and metastatic neoplasms.

EXAMPLE 2

Toso Inhibits Fas-, TNFα- and FADD-Induced Apoptosis

Figure 4:
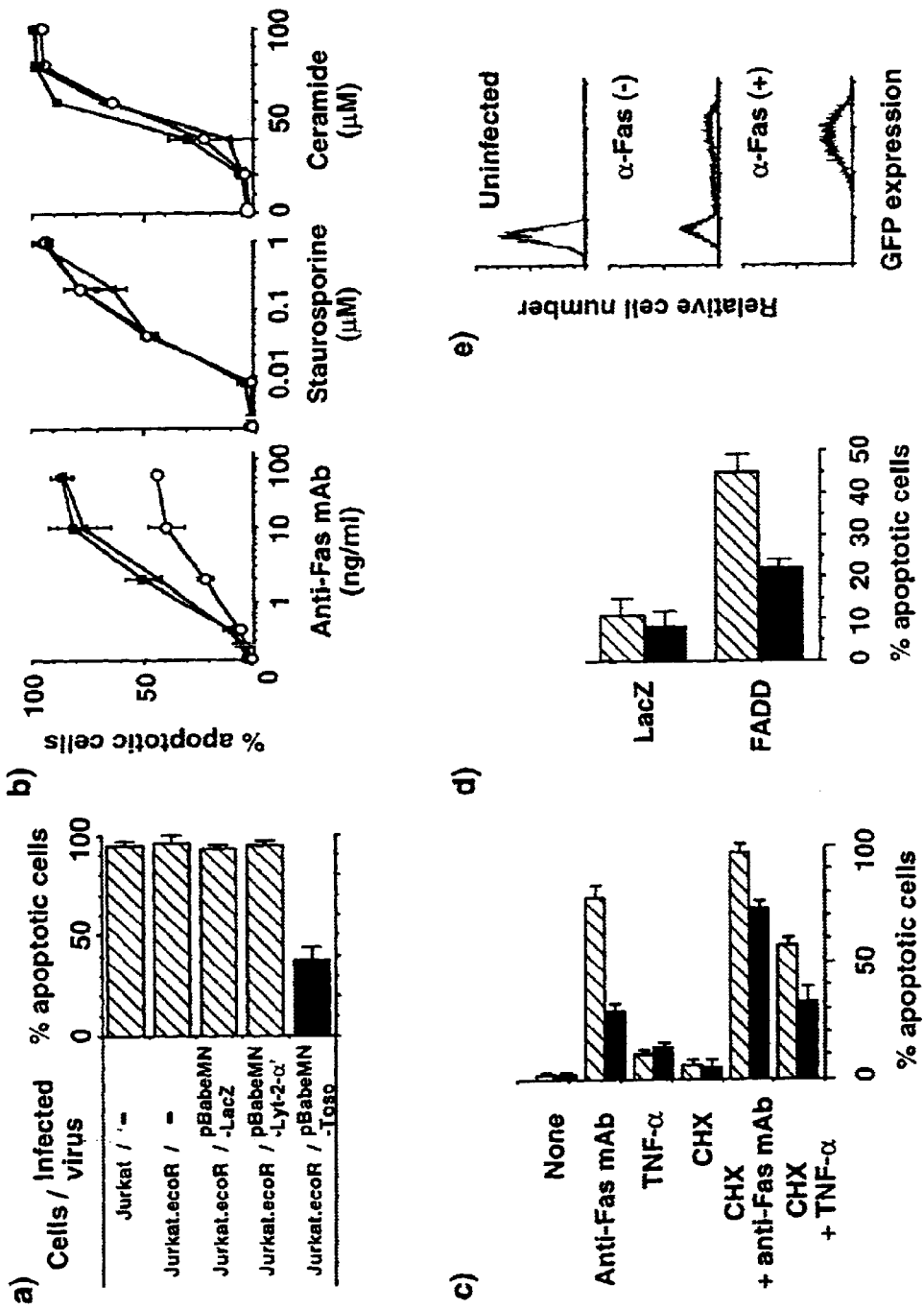
FIG. 4a depicts the effect of Toso on anti-Fas induced apoptosis. The percentage of apoptotic cells are expressed as the mean (hatched and shaded bar)±SD of triplicate cultures. Apoptotic cells in each culture without anti-Fas mAb were less than 2%.
FIG. 4b depicts the effect of Toso on anti-Fas-, staurosporine- and ceramide-induced apoptosis in Jurkat.ecoR cells (closed triangle), Jurkat.ecoR cells infected with pBabeMN-lacZ (closed square) and pBabeMN-Toso (open circle). The percentage of apoptotic cells are expressed as the mean (symbol)±SD (vertical bar) of triplicate cultures.
FIG. 4c depicts the effect of Toso on FADD-induced apoptosis in Jurkat.ecoR cells infected with pBabeMN-Lyt-2-α' (hatched bar), and pBabeMN-Toso (shaded bar). The percentage of apoptotic cells are expressed as the mean (hatched bar or shaded bar)±SD of triplicate cultures.
FIG. 4d depicts the effect of Toso on TNF-α-induced apoptosis in Jurkat.ecoR cells. The percentage of apoptotic cells are expressed as the mean (hatched bar or shaded bar)±SD of triplicate cultures.
FIG. 4e depicts the effect Toso on anti-Fas mAb-induced apoptosis in cells cultured with (α-Fas (+)) or without (α-Fas (−)) 50 ng/ml of anti-Fas mAb. After culture for five days, GFP expression of survived cells were analyzed by FACScan.

Jurkat cells that express the receptor for ecotropic murine retroviruses ("Jurkat.ecoR") were infected with retroviruses that express Toso and control vectors, pBabeMN-Toso, pBabeMN-lacZ and pBabeMN-Lyt-2-α' (α' form of mouse CD8α chain) (Tagawa, et al. (1986)). Cells were cultured in the presence of several reagents such as anti-Fas mAb (Kamiya Biomedical Company), staurosporine (SIGMA Chemical Company, MO 63178, U.S.A.), ceramide (SIGMA), PMA (SIGMA)/Ionomycin (SIGMA), human TNF-α (R&D systems, Minneapolis, Minn. 55413)/Cycloheximide (SIGMA). After 12 or 24 hours, the cells were stained with 100 µg/ml ethidium bromide (SIGMA) and 100 µg/ml acridine orange (SIGMA). Apoptotic cells and non-apoptotic cells were identified with UV microscopy as described (MacGahon, et al., *The End of the (Cell) Line: Methods for the Study of Apoptosis in vitro*, in Methods in cell biology, L. J. Schwartz and B. A. Osborne, eds., San Diego, Calif., Academic Press, Inc., pp. 172–173 (1995)). For FADD-induced apoptosis, mouse FADD (a gift from Dr. Angeles Estelles, Dept. Mol. Pharm., Stanford Univ.) was ligated into pBabeMN retroviral vector. Jurkat.ecoR cells expressing Lyt-2-α' or Toso were infected with pBabeMN-LacZ or pBabeMN-FADD. After 24 hours infection with FADD, the cells were stained with ethidium bromide and acridine orange and counted the apoptotic cells. Jurkat.ecoR cells were infected with pBabeMN-lacZ, pBabeMN-Lyt-2-α', and pBabeMN-Toso. At 72 hours postinfection, infection frequency of pBabeMN-lacZ and pBabeMN-Lyt-2α' were determined to be 45% and 58%, respectively. Jurkat cells were then cultured with 10 ng/ml anti-Fas mAb for 24 hours and apoptotic cells were counted. Jurkat.ecoR cells expressing Toso were resistant to apoptosis induced by 10 ng/ml of anti-Fas mAb, whereas Jurkat cells, Jurkat.ecoR cells and Jurkat.ecoR cells that expressed lacZ or Lyt-2-α', all succumbed to apoptotic death (FIG. 4a).

Staurosporine is a bacterial alkaloid that is a broad spectrum inhibitor of protein kineses (Tamaoki and Nakano, *Biotechnology*, 8:732–735 (1990)) and induces programmed cell death in various cell lines and dissociated primary cells in culture (Ishizaki, et al., *J. Cell Biol.*, 121:899–908 (1993); Jacobson, et al., *Nature*, 361:365–369 (1993); Raff, et al., *Science*, 262:695–700 (1993)). Ceramide generation is implicated in a signal transduction pathway that mediates programmed cell death induced by Fas and TNF-α (Cifone, et al., *J. Exp. Med.*, 180:1547–1552 (1994); Obeid, et al., *Science*, 259:1769–1771 (1993)). pBabeMN-LacZ infected cells were counted by microscopic observation; infection frequency was determined to be 57%. At 72 hours postinfection, Jurkat.ecoR cells and Jurkat.ecoR cells infected with pBabeMN-lacZ and pBabeMN-Toso were cultured with anti-Fas mAb, staurosporine and ceramide for 24 hours. Although Jurkat.ecoR cells expressing Toso were resistant to Fas-mediated apoptosis over a range of antiFas dilutions, these cells were not resistant to any concentration of staurosporine- or ceramide-induced apoptosis (FIG. 4b).

The Fas receptor has homology to the TNF-α receptor, and these two receptors share analogous signaling systems as well as several intracellular mediators (Hsu, et al., *Cell* 84:299–308 (1996)). The protective effect of Toso against TNF-α-induced apoptosis was tested by culturing Jurkat.ecoR cells expressing Lyt-2-α' or Toso with 10 ng/ml of anti-Fas mAb or 1 µg/ml of TNF-α in the presence of 0.1 µg/ml of cyclohexamide (CHX) for 12 hours and apoptotic cells were counted. The infection frequency of pBabeMN-Lyt-2-α' was determined to be 58%. Toso inhibited Fas induced apoptosis in the presence of CHX and also protected against TNF-α-induced apoptosis in comparison to Jurkat.ecoR expressing Lyt-2-α' (FIG. 4d). Thus the TNF-α and Fas signaling pathways may converge at a common point that can be inhibited by Toso.

Fas-mediated Apoptosis Is Activated through FADD

The effect of Toso on FADD-induced apoptosis was investigated by infecting Jurkat.ecoR cells expressing Lyt-2-α or Toso, with pBabeMN-LacZ or pBabeMN-FADD. The reinfection efficiency was approximately 40% using pBabeMN-LacZ. Jurkat.ecoR cells were infected with pBabeMN-Lyt-2-α', and pBabeMN-Toso. Infection frequency of pBabeMN-Lyt-2-α' was determined to be 72%. Jurkat.ecoR cells expressing Lyt-2-α' or Toso were infected with pBabeMNLacZ or pBabeMN-FADD and apoptotic cells were counted at 24 hours postinfection. Infection frequency of pBabeMN-lacZ in Jurat.ecoR cells expressing Lyt-2-α' and Toso was determined to be 39% and 43%, respectively. As shown in FIG. 4c, FADD induced apoptosis in 45% of control Jurkat cells. However, FADD failed to induce apoptosis in Jurkat.ecoR cells constitutively expressing Toso.

The downstream effects of Toso on known inhibitors of apoptosis, were evaluated by western blot analysis of Bcl-2 and BCI XL expression levels in Toso expressing cells. For detection of Toso or deletion mutants that has a HA tag, whole-cell lysates ($2 \times 10^5$ cells per lane) were resolved by SDS-PAGE, transferred to an Immobilon-P transfer membrane (Millipore, Bedford, Mass. 01730, U.S.A.) and processed using ECL western blotting analysis system (Amersham Life Science, Arlington Heights, Ill. 60005, U.S.A.) with Mouse monoclonal anti-hemagglutinin antibody (HA.11) (Babco, Richmond, Calif. 94804, U.S.A.) as per manufacturer recommendation. Bcl-2 overexpression can block Fas-induced apoptosis as well as staurosporine-induced apoptosis (data not shown). No change in the levels of expression of Bcl-2 or BCI XL was observed by Western blot (data not shown). Thus, it appears that intracellular signaling events generated by FADD can be directly and efficiently blocked by signals emanating from Toso at a point prior to engagement of Bcl-2 and BCI XL. The results also suggest that Toso's effect is not due to down regulation of FADD gene expression.

Figure 5:
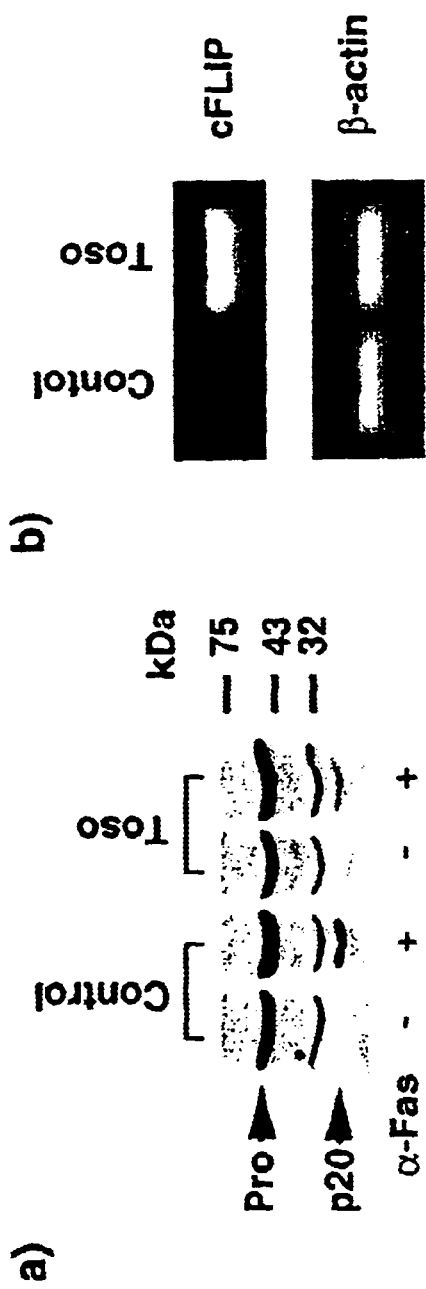
FIG. 5a depicts the results of Western blot analysis of caspase-8 processing by induction of cFLIP. Jurkat.ecoR cells (control) and pBabeMN-Toso-infected Jurkat.ecoR cells (Toso) were cultured with (+) or without (−) 50 ng/ml of anti-Fas mAb (α-Fas) for 6 hours. Positions of procaspase-8 (Pro), the processed form (p20) and standard marker are indicated.
FIG. 5b depicts the results of Western blot analysis of cFLIP expression in Jurkat.ecoR cells (control) and pBabeMN-Toso-infected Jurkat.ecoR cells (Toso).

The effect of overexpression of Toso on processing of caspase-8, which associates with FADD, was evaluated. The processed form (p20) of FLICK after Fas activation was greatly reduced in pBabeMN-Toso-infected Jurkat.ecoR cells in comparison with control Jurkat.ecoR cells (see FIG.

a). To detect caspase-8, whole-cell lysates (2×10⁶ cells per lane) were resolved by SDS-PAGE, transferred to an membrane and processed with goat anti-Mch5 p20 antibody (Santa Cruz Biotechnology, Inc., Santa Cruz, Calif. 95060, U.S.A.) as described above. This data indicates that Toso inhibits caspase-8 processing after Fas activation. cFLIP expression was induced by Toso (FIG. 5b). These results strongly suggest that the extracellular domain of Toso inhibits Fas-induced apoptosis by preventing caspase-8 processing through cFLIP upregulation. Toso did not inhibit staurosporine-induced programmed cell death and staurosporine has been shown to activate caspase-8 (Jacobsen, et al., *J. Cell Biol.*, 133:1041–1051 (1996)). Therefore, additional Toso effects do not occur downstream, nor at the level, of caspase-8. Supporting this, Toso also did not inhibit ceramide-induced apoptosis, which acts downstream or independent of caspase-8 as demonstrated in experiments using the caspase-8-specific inhibitor peptide, DEVD-CHO (Gamen, et al., *FEBS Lett.*, 390:232–237 (1996)), which does not inhibit ceramide-induced apoptosis. Overexpression of Bcl-2 or Bcl-XL is known to prevent apoptosis in response to ceramide and staurosporine (Geley, et al., *FEBS Lett.*, 400:15–18 (1997); Susin, et al., *J. Exp. Med.*, 186:25–37 (1997); Takayama, et al., *Cell*, 80:279–284 (1995); Zhang, et al., *Proc. Natl. Acad. Sci. USA*, 93:5325–5328 (1996)). Toso did not change the expression levels of Bcl-2 nor BCL-XL in Jurkat cells, showing that neither Bcl-2 nor BCL-XL were involved in the protective activities of Toso. Taken together then, Toso activates an inhibitory pathway that prevents caspase-8 activation following Fas stimulation through upregulation of cFLIP, and not by blocking apoptotic signals downstream or at the level of caspase-8. This explains the apparent specificity of the blockade to TNF family-related surface receptors that use caspase-8 for apoptotic signaling.

Cells expressing Toso alone were mixed with an equal number of cells expressing lacZ. After one round of Fas stimulation, no lacZ-expressing cells remained as assayed by X-gal. In addition, Jurkat.ecoR cells were infected with pBabeMN-Toso-IRES-GFP. After infection, cells were cultured with (α-Fas (+)) or without (α-Fas (−)) 50 ng/ml of anti-Fas mAb. In the absence of anti-Fas mAb treatment (Fas (−))., 46% GFP negative cells and 54% GFP positive cells were observed in pBabeMN-Toso-IRES-GFP-infected Jurkat.ecoR cells. After five days culture with anti-Fas mAb, survivors were obtained from pBabeMN-Toso-IRES-GFP-infected Jurkat.ecoR cells, but not from control pBabeMN-IRES-GFP-infected Jurkat.ecoR cells (data not shown); 99.7% of surviving Jurkat cells expressed GFP as shown in FIG. 4e (Fas(+)). These data indicate that cells that express the extracellular domain of Toso are protected from Fas-induced apoptosis and suggests that Toso does not exert its effect as a secreted form.

EXAMPLE 3

The Immunoglobulin Domain and the Transmembrane Region of Toso Are Required for Inhibition of Fas-induced Apoptosis The C-terminus deletion mutants (TosoΔ(377–390).HA, TosoΔ(334–390).HA, TosoΔ(281–390).HA and TosoA(252–390).HA), the N-terminus deletion mutant (TosoΔ(29–187).HA) and the fusion protein (Lyt-2/Toso(271–390).HA) of the extracellular domain and transmembrane region from Lyt-2-α' and the cytoplasmic domain from Toso, which have the influenza virus hemmagglutinin tag (HA) in C-terminus, were generated by. Primers in the antisense orientation, carrying the 20 nucleotide sequences of Toso located upstream of the deletion sites, HA tag sequence and an in-frame termination codon, as well as NcoI site, were synthesized. The DNA fragment of the Toso gene from the XhoI site located in the extracellular domain to the NcoI site that is located in 3' non-coding region was replaced with the PCR products amplified from pBabeMN-Toso using LibS and each primer described above. A primer for TosoΔ(29–187).HA in the antisense orientation carrying the 20 nucleotides located after the leader peptides of Toso and XhoI site was synthesized. The DNA fragment from DraIII site, which is located 190 bp upstream of cDNA insert cloning sites, to XhoI site in pBabeMN-Toso.HA was replaced with the PCR product amplified from pBabeMN-Toso using LibS and the primer. For Lyt2/Toso(271–390).HA, primer in sense orientation which is carried a BamHI site and the 20 nucleotides located upstream of the cytoplasmic domain was synthesized. The DNA fragment from Bcl I site, which is located in the end of transmembrane region of Lyt-2-α', to SalI site, which is located downstream of Lyt-2-α' cloning sites in pBabeMN-Lyt-2-α', was replaced with the PCR product amplified from pBabeMN-Toso.HA using LibA and the primer. All mutants generated by PCR were verified by DNA sequencing using cycle sequencing ready reaction kit. Toso deletion mutants prepared as described above were epitope-tagged in order to delineate the regions responsible for anti-apoptotic signal transduction, (FIGS. 6a and 6b). Toso.HA (fused to the hemagglutinin, HA, tag) had an apparent molecular weight of 60 kDa, suggesting Toso is heavily glycosylated. The cell surface expression of Fas using anti-human Fas mAb, CH11, was determined by FACS to explore whether Toso has an effect on Fas expression. Fas was expressed at similar levels on the surface of cells expressing either full-length Toso, Toso deletion mutants, or control vector. Thus, the extracellular domain of Toso neither downregulates Fas, nor directly interferes with the ability of the antibody to bind and presumably stimulate Fas.

Figure 3:
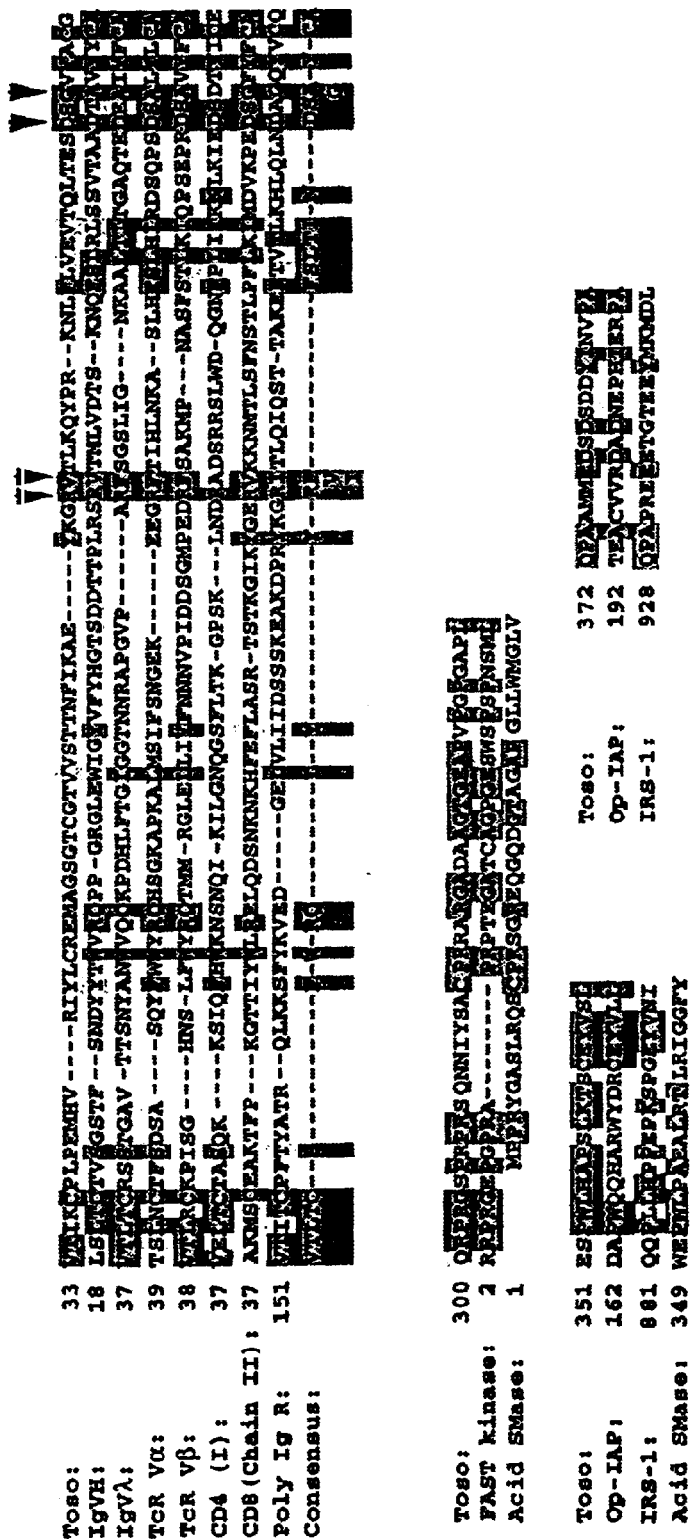
FIG. 3 (SEQ ID NOS:3–21) depicts BLAST search results using the Toso gene product. The position of the first amino acid in each sequence is given in the left side of the alignment. Gaps are indicated by dashes. Dark and light shading refer to identical and similar residues, respectively. For sequence alignment of the Toso N-terminus, IgVH (G1HUNM), IgVλ (L1MS4E), TcR Vα (RWMSAV), TCR Vβ (RWHUVY), CD4 (U47924), CD8 chain 11 (X04310), Poly Ig R (QRRBG) and immunoglobulin V-set consensus sequence are shown in the alignment. Arrows indicate positions characteristic of many V-set sequences. The sequence of the Toso cytoplasmic domain is aligned with acid sphingomyelinase, insulin receptor substrate 1 (IRS1) and apoptosis inhibitor, IAP, from *Orgyia pseudolsugata* nuclear polyhedrosis virus (Op-1AP).

Jurkat.ecoR cells were infected with pBabeMN-Lyt-2-α'.HA, pBabeMN-Toso. HA, pBabeMN-TosoΔ(377–390).HA, pBabeMN-TosoΔ(334–390). HA, pBabeMN-TosoΔ(281–390).HA, pBabeMNTosoΔ(252–390).HA and pBabeMN-TosoΔ(29–187).HA. Jurkat cells were cultured with 10 ng/ml anti-Fas mAb for 24 hours and apoptotic cells were counted. Apoptosis was readily induced in control Jurkat.ecoR cells and Jurkat.ecoR cells expressing Lyt-2-α'.HA, whereas apoptosis was markedly inhibited in Jurkat.ecoR cells that expressed Toso.HA (FIG. 6a). Deletions of regions of the cytoplasmic domain of Toso from 334 to 390 still inhibited apoptosis. Moreover, a deletion of Toso lacking the entire cytoplasmic domain still retained substantial anti-apoptotic ability. Thus, the cytoplasmic domain of Toso is not absolutely required for the anti-apoptotic effects on Fas antibody-stimulated cells. (See Example 5, below) These results indicate that the homologies observed in the cytoplasmic region of Toso, as shown in FIG. 3, are not the only sources of the anti-apoptotic signals generated by a Toso complex, although the cytoplasmic regions are required for enhancing the anti-apoptotic effects of Toso.

The Toso mutant lacking the tnansmembrane and cytoplasmic domains demonstrated that inhibition of Fas-induced apoptosis by Toso requires its insertion into membranes. As shown in FIG. 6a, soluble TosoΔ(252–390).HA afforded no protection from apoptosis. Expression of the TosoΔ(252–390).HA protein was confirmed by western blot analysis of culture supernatants. Supernatants derived from pBabeMN-TosoA(252–390). HA-transfected 293T cells did not inhibit Fas-induced apoptosis, indicating that a membrane-proximal event dependent on cis-localization of Toso is required for blockade of the Fas-mediated death signal.

Many cell surface receptor complexes act through oligomerization and most immunoglobulin (Ig) domain proteins exist in homodimeric and heterodimeric Ig forms, functioning as self-assembling systems. Disruption of the Ig domain of Toso completely abrogated the anti-apoptotic ability of Toso (TosoΔ(29–187).HA). (See FIG. 6a). Further, a chimeric Lyt-2Toso fusion protein in which the cytoplasmic domain of Toso was coupled to the extracellular and transmembrane region of Lyt-2-α' (α' form of murine CD8α, which forms homodimers at the cell surface) (Tagawa, et al., (1986)) failed to inhibit Fas-induced apoptosis. Furthermore, anti-mouse CD8a mAb (Lyt-2) was used to crosslink the Lyt-2-Toso chimeras and induce multimerization of the Toso cytoplasmic domains. Toso.HA-expressing Jurkat.ecoR cells ($5 \times 10^6$ cells) were incubated with 2 mM BS3 (PIERCE, Rockford, Ill. 61105, U.S.A.) for 1 hour at 4° C. After incubation, 1M Tris-HCl was added to a final concentration of 10 mM and cells were incubated for 15 minutes at 4° C. Whole-cell lysates were resolved by SDS PAGE, transferred to a membrane and processed with mouse monoclonal antihemagglutinin antibody (HA. 11) (Babco) as described above. Jurkat.ecoR cells and Toso-expressing Jurkat.ecoR cells were used as controls. Jurkat.ecoR cells which expressed the chimeric Lyt-2-Toso fusion protein did not show any protection against anti-Fas mAb-induced apoptosis in presence of anti-mouse CD8α mAb. These results suggest that some form of Ig domain mediated dimerization of Toso is required to initiate the anti-apoptotic effect in conjunction with the cytoplasmic region of Toso or other cell surface Toso-associating proteins. Cell surface molecules on Toso.HAexpressing Jurkat.ecoR cells were crosslinked using the water-soluble crosslinker, BS3 and apparent crosslinking molecular complexes at 150, 240, 300 kDa were detected (See FIG. 6c). This result first indicates that Toso is a surface expressed receptor. The results are consistent with an association of Toso with another surface protein(s) of molecular weight 90 kDa. The several molecular weights observed for the crosslinked complexes are also minimally consistent with stochiometric mixtures of 60 and 90 kDa molecules.

Domain Analysis of Toso Suggests Multiple Interacting Partners

Deletion analysis of Toso indicated that surface expression of the immunoglobulin V-like region is necessary to inhibit Fas-induced-apoptosis and that the cytoplasmic domain of Toso is insufficient and indeed partly expendable for the anti-apoptotic function. Deletion of the cytoplasmic domain resulted in abrogation of only about half of the anti-apoptotic effect. This suggests that Toso must be expressed at the cell surface in a manner where it presumably interacts other surface molecule(s) that propagate an anti-apoptotic signal. Most immunoglobulin family receptors are homo- or heterodimers that can become activated through ligand interactions. Crosslinking experiments revealed multiple potential higher-order complexes (150, 240, and 300 kDa), suggesting at least one partner of 90 kDa that interact with Toso. We suspect that Toso forms a heterodimer with this other surface protein to collaborate in initiating the anti-apoptotic signal that leads to cFLIP induction. Interactions of surface-expressed Toso complexes with ligands on or near target cells might also modulate the ability of Toso to provide anti-apoptotic signaling. We are currently investigating the existence of such ligands and contributory molecules.

A model summarizing the results is shown in FIG. 10. In this model, stimulation through of the T cell receptor complex transmits activation signals leading to upregulation of Fas and FasL. Activation also induces Toso expression, providing the potential for anti-apoptotic signals that protect against Fas-mediated apoptosis. Toso accomplishes this by forming homo- or heterodimers at the cell surface to generate signals that inhibit the initiation or propagation of caspase-8 activation by cFLIP. It is also possible that Toso requires an extracellular ligand that might modulate its activities. The signaling pathway activated by Toso is clearly important as it leads to induced expression of cFLIP (Irmler, et al. (1997); Srinivasula, et al. (1997)).

EXAMPLE 4

T Cell Signaling Leading to Apoptosis Is Blocked by Activated Toso

Poly (A)$^+$ RNA was prepared from Jurkat cells or Jurkat cells stimulated for 24 hours with 10 ng/ml of phorbol 12-myristate 13-acetate (PMA; SIGMA Chemical Company, MO 63178, U.S.A.) and 1 μg/ml phytohemagglutinin (PHA; SIGMA) or 10 ng/ml PMA and 500 ng/ml Ionomycin (SIGMA). Poly (A)$^+$ RNA (5 μg) was subjected to electrophoresis through 1% agarose gel containing 2.2 M formaldehyde, and transferred to Hybond N$^+$ membrane (Amersham Life Science Inc., IL 60005, U.S.A.). Hybridization was carried out according to the manufacturer's recommendation. A specific probe for the Toso coding region (1.2 kbp) was synthesized with PCR from pBabeMN-Toso using 5'-AGG GGC TCT TGG ATG GAC (SEQ ID NO:26) (TosoS) and 5'-CTG GGG TTG GGG ATA GC (SEQ ID NO:27) (TosoA). As a control probe, the human β-actin cDNA control probe (CLONTECH Laboratories, Inc., CA 94303-4230) was used. Probes were labeled with $^{32}$p using a random-primed labeling kit, Prime-a-Gene (Promega). Human RNA Master Blot and Human Immune System Multiple Tissue Northern Blot II (CLONTECH Laboratories) were used to survey Toso mRNA expression in several human tissues. Toso expression was observed in lymph nodes, lung and kidney. In addition to these tissues, we detected faint signals from spleen, thymus, liver, heart and salivary gland. Tissues which were analyzed for Toso mRNA include: A1: Whole brain, A2: Amygdala, A3: Caudate nucleus, A4: Cerebellum, A5: Cerebral cortex, A6: Frontal lobe, A7: Hippocampus, A8: Medulla oblongata, B1: Occipital lobe, B2: Putamen, B3: Substantia nigra, B4: Temporal lobe, B5: Thalamus, B6: Subthalamic nucleus, B7: Spinal cord, C1: Heart, C2: Aorta, C3: Skeletal muscle, C4: Colon, C5: Bladder, C6: Uterus, C7: Prostate, C8: Stomach, D1: Testis, D2: Ovary, D3: Pancreas, D4: Pituitary gland, D5: Adrenal gland, D6: Thyroid gland, D7: Salivary gland, D8: Mammary gland, E1: Kidney, E2: Liver, E3: Small intestine, E4: Spleen, E5: Thymus, E6: Peripheral leukocyte, E7: Lymph node, E8: Bone marrow, F1: Appendix, F2: Lung, F3: Trachea, F4: Placenta, G1: Fetal brain, G2: Fetal heart, G3: Fetal kidney, G4: Fetal liver, G5: Fetal spleen, G6: Fetal thymus, G7: Fetal lung. (FIG. 7a). Using Human Immune System Multiple Tissue Northern Blot II, and film exposed at –70° C. with an intensifying screen for one day, endogenous Toso mRNA species of 2.0 (major), 2.8, 3.5 and 4.3 kbp were detected in lymph node and spleen (see FIG. 7b). The nucleotide length of the cDNA was 1.9 kbp, suggesting that the additional bands might either be alternative splice products or incompletely processed messages. Toso expression was also observed in peripheral blood leukocytes, thymus (FIG. 7b). Expression in bone marrow and fetal liver was much lower than that in lymph node and spleen, as seen after overexposure of the blot (data not shown).

The expression of Toso in several human cell lines was analyzed by semi-uantitative RT-PCR involving amplification of the 1.2 kbp-coding region of Toso (FIG. 7c). The first strand of cDNA was synthesized with 10 µg total RNA from several human cell lines and peripheral blood mononuclear cells. PCR was performed for 35 cycles using TosoS and TosoA. After an initial denaturation at 94° C. for 5 minutes, each cycle of amplification consisted of 30 second denaturation at 94° C., followed by a 30 second-annealing at 58° C. and 2 minutes extension at 72° C. After 35 cycles, the final product was extended for 10 minutes at 72° C. PCR products were electrophoresed through 1.0% agarose gel and transferred to Hybond N+ membrane. The BamHI-Xhol fragment (510 bp) of the Toso-coding region were labeled with $^{32}$p. Hybridization was carried out as described above. To detect cFLIP mRNA expression, a 1.1 kbp fragment (998–2061) of the cFLIP gene (U97074) was amplified with primers 5'-GGG AGA AGT AAA GAA CAA AG (SEQ ID NO:28) and 5'-CGT AGG CAC AAT CAC AGC AT (SEQ ID NO:29) for 35 cycles as described above. The sequence of the 1.1 kbp PCR product was verified using cycle sequencing ready reaction kit (Perkin Elmer, CA 94404, U.S.A.). As a control, β-actin cDNA was amplified for 15 and 25 cycles as described above.

Toso mRNA was detected in lymphoid cell lines such as Jurkat cells (T cell leukemia), a kind gift from Dr. Kuo, Harvard Univ., Cem T4 cells (T cell leukemia), MolT-4 cells (T cell leukemia), HB11.19 cells (B cell lymphoma), a kind gift from Dr. Cleary, M. L., Stanford Univ., and Reh cells (acute lymphocytic leukemia; non T; non B, ATCC). HL-60 cells (promyelocytic leukemia, ATCC) displayed a consistently weak signal. In contrast, Toso PCR products were not detected in non-hematopoietic cell lines including HepG2 cells (hepatoblastoma, a kind gift from Dr. Blau, Stanford Univ.), 293 cells (kidney; transformed with adenovirus, ATCC) and Hela cells (cervix; adenocarcinoma, ATCC). Toso therefore is constitutively expressed in cells of hematopoietic cells.

Poly (A)⁺ RNA was prepared from Surkat cells stimulated for 24 hours with 10 ng/ml PMA (SIGMA) and 500 ng/ml lonomycin (SIGMA). The first strand of cDNA was synthesized with 10 µg Poly (A)⁺ RNA using oligo-dt primers and performed PCR with primers, 5'-A<u>GA ATT CTC</u> TCT AGG GGC TCT TGG ATG (SEQ ID NO:30) (See FIG. 1 where the EcoRI site is underlined) and 5'-ATA <u>AAG CTT</u> CTC AGG GCA CAG ATA GAT GG (SEQ ID NO:31) (HindIII site is underlined), which were located 23 bp and 136 bp nucleotides upstream and downstream of the Toso coding region, respectively. The 1.3 kbp fragment was ligated into pBluescript SK(+). Five independent clones were picked up and sequenced using cycle sequencing ready reaction kit (Perkin Elmer). The deduced amino-acid sequences from the five independent clones were completely identical to the gene from the cDNA library screening, although two silent mutations were found within the original gene as compared to the PCR consensus sequences.

Toso was expressed in several human cell lines including Jurkat cells, CemT4 cells (human T cell leukemia), SupT1 cells (human T cell leukemia, a kind gift from Dr. Cleary, M. L., Stanford Univ.), Oli-Ly8 cells (human B cell line; transformed with EBV), AMK cells (human B cell line; transformed with EBV), both a gift from Dr. Negrin, R. S., Stanford Univ., Reh cells (acute lymphocytic leukemia; non T; non B), HL-60 cells (promyelocytic leukemia) and HepG2 cells (hepatoma) using pBabeMN-Toso IRKS neo to allow cotranslational selection with Geneticin (GIBCO BRL). All of the human T cell lines and one of the human B cell lines, Oil-Ly8 cells, in which Toso was overexpressed, were inhibited for apoptosis induced by anti-Fas mAb, whereas no significant protection was observed against Fas-induced apoptosis in the other cell lines (data not shown). Thus, the anti-apoptotic effect of Toso also is limited to certain classes of hematopoietic cells, suggesting the presence of tissue-specific mediators in these cells.

T cell activation results in increased expression of Fas and FasL on the cell surface. This is paradoxical, as it is clear that T cells do not kill themselves after such induction, whereas overexpression of Fas and FasL in other cell types does lead to cell death. In vitro, PMA and lonomycin can induce apoptosis in T cells (Oyalzu, et al., *Biochem. Biophys. Res. Commun.*, 213:994–1001 (1995)) by mimicking certain aspects of CD3 engagement, including upregulation of Fas and FasL. One function of Toso might be to inhibit T cell activated self-killing and that the levels of Toso might become increased following T cell activation, helping to render Jinkat cells partially resistant to upregulated Fas and FasL. Expression of Toso mRNA in Jurkat cells was examined by northern hybridization. As shown in FIG. 8a, an endogenous Toso mRNA species of 2.8 kbp was detected in resting Jurkat cells, although expression was seen after overexposure of the blot (data not shown). Toso mRNA expression increased, including minor species (2.0, 3.5, 4.3, 5.5 kbp), after stimulation of Jurkat cells with PMA and PHA (15-fold increase) or PMA in combination with lonomycin (25-fold increase). Thus, Toso can be induced following T-cell activation.

Jurkat.ecoR cells, JurkaL.ecoR cells infected with pBabeMN-lacZ, and pBaeMN-Toso-infected clones were precultured with 10 ng/ml PMA and 500 ng/ml Ionomycin for 12 hours and then incubated with 10 ng/ml of anti-Fas mAb for 24 hours, and as shown in FIG. 8b, Jurkat cells were susceptible to anti-Fas mAb-induced apoptosis as well as PMA/lonomycin-induced apoptosis. However, following activation with PMA/lonomycin one third of Jurkat cells were clearly resistant to anti-Fas mAb induced apoptosis. These results suggest that Jurkat cells activate a protective system that blocks Fas-mediated apoptosis, supporting the contention that induced Toso is a mediator in this protective effect.

We further tested whether Toso expression could rescues activation-induced programmed cell death. We randomly picked five pBabeMN-Toso-infected Fas resistant Jurkat T cell clones and used these to assay the inhibitory effect of Toso on PMA/lonomycin-induced apoptosis. All five clones exhibited significant resistance to PMA/lonomycin-induced apoptosis, as well as continued strong resistance to Fas-induced apoptosis (FIG. 8c). Control clones displayed the expected killing effect when activated with PMA and lonomycin. Toso not only inhibited apoptosis activated by Fas and TNF-α, but also inhibited apoptosis induced by certain classes of T cell activation events.

Normal T cells at early stages of activation are resistant to Fas-induced apoptosis but become Fas sensitive at late stages of activation (Klas, et al., (1993)). Toso expression kinetics in peripheral blood mononuclear cells were examined after PHA stimulation using by semi-quantitative RT-PCR. Peripheral blood leucocyte (PBL) from healthy volunteers were isolated by Histopaque-1077 (Sigma) density centrifugation. Adherent cells were removed by adherence to plastic culture vessels. Cells were activated with phytohemagglutinin (PHA)-P (1 µg/ml) for 24 hours washed, and cultured with 20 U/ml of recombinant human IL-2 (R&D Systems Inc., Minneapolis, Minn. 55413, U.S.A.). To perform mixed lymphocyte culture, PBL were treated with 20 µg/ml of mitomycin-C (stimulating cells, SC) for 3 hours and washed. SC were adjusted to 7×10⁵ cells/ml and cultured with an equal volume and cell density of PBL (responding cells, RC) from another donor (Clot, et al., *Immunology*, 29:445–453 (1975)). Cells were cultured for one to seven days (day 1, 3, 5, and 7). Toso expression was observed at day 1 and upregulated expression at day 3 after activation. However, Toso expression was clearly decreased at days 5 (FIG. 9*a*), correlating with Fas sensitivity studies (Klas, et al. (1993)). Further, allogenic stimulation in mixed lymphocyte cultures was performed to determine whether Toso is activated in prim immune cells upon T cell activation. As shown in FIG. 9*b*, Toso expression was also rapidly induced in the presence of stimulator cells on day 1; however Toso expression in mixed Iymphocyte cultures was reduced by day 6 to levels even lower than seen on day 1 and responder cells alone at day 6. These results further confirm a supportive role for Toso induced resistance to Fas-mediated death during T Iymphocyte activation.

Natural T cell resistance to Fas-induced apoptosis shows a time-dependent kinetics (Klas, et al. (1993)). By day 6 post-activation, T cells become susceptible to Fas-induced death. In addition, activation of Jurkat cells by PMA/Ionomycin induces a significant increase in Fas ligand expression which is thought to promote apoptosis (Oyalzu, et al. (1995); Brunner, et al., *Nature*, 373:441–444 (1995)). However, PMA/Ionomycin-activated Jurkat cells were not as efficiently induced to undergo apoptosis by anti-Fas mAb treatment compared to unstimulated Jurkat cells (FIG. 8*b*). This suggested that Jurkat cells become at least partly resistant to anti-Fas mAb-induced apoptosis after T cell signaling, mimicking processes observed in natural T cells. mRNA expression of Toso in Jurkat cells, as well as in peripheral T cells, is strongly upregulated upon stimulation with T cell activators. Further, overexpression of Toso protected Jurkat cells against PMA/Ionomycin- induced apoptosis.

This is consistent with the proposal that Toso expression, which transiently increased and then decreased in peripheral blood mononuclear cells after activation with PHA or allogenic stimulation, is responsible for the temporary Fas resistance in T cells. Hence, the results are consistent with the hypothesis that Toso may be involved in activation-induced resistance to apoptosis of T cells during an immune response. We conclude from the results that the inhibitory effect of the extracellular domain of Toso in activation-induced apoptosis is attributable to the inhibition of Fas-mediated signal transduction through inhibition of caspase-8 by c-FLIP induction.

The finding that Toso can exert cell-specific and signaling pathway specific effects on apoptosis suggests that other polypeptides exist that act upon the Fas death induction cascade. Critically, the fact that signaling by the extracellular domain of Toso induces expression of cFLIP suggests the existence of a regulatable transcription cascade that can be activated to block Fas-mediated apoptosis in some cell types. As shown here, high efficiency gene transduction using a retroviral approach, like other cDNA cloning approaches (Vito, et al., *Science*, 271:521–525 (1996); Kitamura, et al., *Prac. Natl. Acad. Sci.*, 92:9146–9150 (1995)), allows functional cloning of genes with high throughput and accuracy. Further analysis of the Toso pathway coupled with gene disruption analysis in animals will further clarify the overall role that the extracellular domain of Toso plays in modulating activation-induced T-cell apoptosis in vivo.

EXAMPLE 5

The Cytoplasmic Domain of Toso Promotes Cell Death in Murine pre-B Cells

70Z/3 cells were incubated with virus at 32° C. for 12 hours including initial spinning and achieved 70–80% infection efficiency estimated using FACS analysis for pBabeMN-Lyt-2O. 70Z3 cells kept about 80% viability at the end of 12 hours incubation with virus. However, after infection, we observed rapid cell death (about 70% of cells were dead) in 70Z/3 cells infected with pBabeMN-TOSO, not in 70 Z3 cells with pBabeMN- Lyt-2O nor with supernatant of φNX-E cells (FIG. 11). Supernatant from pBabeMN-TOSO transfected 293T cells, which is the parental cell line of φNX-E and φNX-A cells, did not induce rapid cell death to 70Z/3 cells. These results suggest that gene products of TOSO induced rapid cell death. Most dead cells after infection showed apoptotic nuclei under microscopic observation, suggesting TOSO induced apoptosis to 70Z/3 cells.

To clarify which region was responsible for apoptotic signal transduction, a set of deletion mutants of the TOSO cDNA was prepared as shown in Example 3. The mutated TOSO cDNA was ligated into pBabeMN retroviral vector and infected 70Z/3 cells. As shown in Table A, below, massive cell death was observed in 70Z/3 cells infected with pBabeMN-TOSO.HA, -TOSOΔ(377–390).HA, -TOSOΔ(334–390). HA and Lyt-2/TOSO(271–390).HA, but not pBabeMN-TOSOΔ(252–390).HA and pBabeMN-TOSOΔ(29–187).HA. Full length Lyt-2 did not induce rapid cell death to 70Z/3 cells after infection (data not shown). Lyt-2/TOSO(271–390).HA. was most effective in promoting cell death in 70Z/3 cells, suggesting that the cytoplasmic region was responsible for massive cell death in 70 Z3 cells.

The TOSO-induced cell death in 70Z/3 cells, suggests that TOSO works not only for protection against Fas-induced apoptosis but also for promotion of cell death. The cytoplasmic domain from $A^{281}$ to $A^{333}$ is responsible for promotion of cell death. BLAST search reveals that this region has partial homology to FAST kinase and acid sphingomyelinase which is involved in Fas-induced apoptosis. When the cytoplasmic domain of TOSO is compared to the "death domain" from several molecules, the cytoplasmic domain of TOSO did not show any homology to known "death domain", including the consensus sequence as described. The promotion of cell death by TOSO was not observed in several cell lines. Cell death induced by TOSO may be observed in some stages of B cell development.

Table A indicates the effect of TOSO deletion mutants on promotion of apoptosis. 70Z/3 cells were infected with pBabeMN-Lyt-2α.HA, pBabeMN-TOSO.HA, pBabeMN-TOSOΔ(377–390).HA, pBabeMN-TOSOΔ(334–390).HA, pBabeMN-TOSOΔ(281–390).HA, pBabeMN-TOSOΔ(252–390).HA and pBabeMN-TOSOΔ(29–187).HA. After infection, the stained cells were incubated with phosphate-buffered saline including 100 μg/ml of ethidium bromide (SIGMA) and 100 μg/ml of acridine orange (SIGMA). Viable cells were identified with UV microscopy. The percentage of viable cells is expressed as mean ± SD of triplicate cultures.

| Infected-Virus Encoding | % Viable Cells |
| --- | --- |
| Lyt-2.HA | 73 ± 5 |
| 4.8.HA | 30 ± 4 |
| 4.8Δ(377-390).HA | 31 ± 5 |
| 4.8Δ(334-390).HA | 29 ± 2 |
| 4.8Δ(281-390).HA | 75 ± 2 |
| 4.8Δ(252-390).HA | 78 ± 3 |
| 4.8Δ(29-187).HA | 83 ± 3 |
| Lyt-2/4.8(271-390).HA | 5 ± 3 |

We claim:

1. An isolated antibody which specifically binds a Toso protein having the amino acid sequence set forth in SEQ ID NO:2.

2. An antibody according to claim 1, wherein said antibody specifically binds to an extracellular domain of of said TOSO protein.

3. An antibody according to claim 1, wherein said antibody specifically binds to a cytoplasmic domain of of said TOSO protein.

* * * * *

UNITED STATES PATENT AND TRADEMARK OFFICE
CERTIFICATE OF CORRECTION

PATENT NO.   : 6,727,350 B2
DATED        : April 27, 2004
INVENTOR(S)  : Nolan, Garry P. et al.

It is certified that error appears in the above-identified patent and that said Letters Patent is hereby corrected as shown below:

Column 1,
Line 4, please insert the following:
-- This invention was made with Government support under contract AI35304 awarded by the National Institutes of Health. The Government has certain rights in this invention. --

Signed and Sealed this

Sixteenth Day of November, 2004

JON W. DUDAS
*Director of the United States Patent and Trademark Office*

SEQUENCE LISTING

<160> NUMBER OF SEQ ID NOS: 31

<210> SEQ ID NO 1
<211> LENGTH: 1910
<212> TYPE: DNA
<213> ORGANISM: Homo sapiens

<400> SEQUENCE: 1

| | | | | | |
|---|---|---|---|---|---|
| aaaggagtaa | gcagcgtgtc | tccatccccc | tctctagggg | ctcttggatg | gaccttgcac | 60 |
| tctagaaggg | acaatggact | tctggctttg | gccactttac | ttcctgccag | tatcaggggc | 120 |
| cctgaggatc | ctcccagaag | taaaggtaga | gggggagctg | ggcggatcag | ttaccatcaa | 180 |
| atgcccactt | cctgaaatgc | atgtgaggat | atatctgtgc | cgggagatgg | ctggatctgg | 240 |
| aacatgtggt | accgtggtat | ccaccaccaa | cttcatcaag | gcagaataca | agggccgagt | 300 |
| tactctgaag | caatacccac | gcaagaatct | gttcctagtg | gaggtaacac | agctgacaga | 360 |
| aagtgacagc | ggagtctatg | cctgcggagc | gggcatgaac | acagaccggg | aaaagaccca | 420 |
| gaaagtcacc | ctgaatgtcc | acagtgaata | cgagccatca | tgggaagagc | agccaatgcc | 480 |
| tgagactcca | aaatggtttc | atctgcccta | tttgttccag | atgcctgcat | atgccagttc | 540 |
| ttccaaattc | gtaaccagag | ttaccacacc | agctcaaagg | ggcaaggtcc | ctccagttca | 600 |
| ccactcctcc | cccaccaccc | aaatcaccca | ccgccctcga | gtgtccagag | catcttcagt | 660 |
| agcaggtgac | aagccccgaa | ccttcctgcc | atccactaca | gcctcaaaaa | tctcagctct | 720 |
| ggaggggctg | ctcaagcccc | agacgcccag | ctacaaccac | cacaccaggc | tgcacaggca | 780 |
| gagagcactg | gactatggct | cacagtctgg | gagggaaggc | caaggatttc | acatcctgat | 840 |
| cccgaccatc | ctgggccttt | tcctgctggc | acttctgggg | ctggtggtga | aagggccgt | 900 |
| tgaaaggagg | aaagccctct | ccaggcgggc | cgccgactg | gccgtgagga | tgcgcgcccct | 960 |
| ggagagctcc | cagaggcccc | gcgggtcgcc | gcgaccgcgc | tcccaaaaca | acatctacag | 1020 |
| cgcctgcccg | cggcgcgctc | tggagcggac | gctgcaggca | caggggaggc | cccgttccc | 1080 |
| ggccccggag | cgccgttgcc | ccccgccccg | ctgcaggtgt | ctgaatctcc | ctggctccat | 1140 |
| gccccatctc | tgaagaccag | ctgtgaatac | gtgagcctct | accaccagcc | tgccgccatg | 1200 |
| atggaggaca | gtgattcaga | tgactacatc | aatgttcctg | cctgacaact | ccccagctat | 1260 |
| cccccaaccc | caggctcgga | ctgtggtgcc | aaggagtctc | atctatctgc | tgatgtccaa | 1320 |
| tacctgcttc | atgtgttctc | agagccctca | tcacttccca | tgccccatct | cgactcccat | 1380 |
| ccccatctat | ctgtggccct | gagcatggct | ctgcccccag | gtcgtcttgc | acaccttggc | 1440 |
| agccccctgt | agttgacagg | taagctgtag | gcatgtagag | caattgtccc | aatgccactt | 1500 |
| gcttcctttc | caagccgtcg | aacagactgt | gggatttgca | gagtgttct | tccatgtctt | 1560 |
| tgaccacagg | gtgttgttgc | tgccaggctc | tagatcacat | ggcatcaggc | tggggcagag | 1620 |
| gcatagctat | tgtctcgggc | atccttccca | gggttgggtc | ttacacaaat | agaaggctct | 1680 |
| tgctctgagt | tatgtgacgt | gcctcagccc | catggactaa | gcagggtct | ggtataaaca | 1740 |
| ctcctggaaa | cgcctttgcc | ctgatccaaa | tgttagcact | tgctagtgaa | cgtctactta | 1800 |
| tctcaagttc | tatgctaaag | gcaatttatc | ttgatgtgat | gataaaccaa | acttattagc | 1860 |
| aagatatgca | tatatatcca | taaattctct | ttactctgtc | tccatccttt | 1910 |

<210> SEQ ID NO 2
<211> LENGTH: 390

```
<212> TYPE: PRT
<213> ORGANISM: Homo sapiens

<400> SEQUENCE: 2

Met Asp Arg Trp Leu Trp Pro Leu Tyr Phe Leu Pro Val Ser Gly Ala
 1               5                  10                  15

Leu Arg Ile Leu Pro Glu Val Lys Val Glu Gly Glu Leu Gly Gly Ser
                20                  25                  30

Val Thr Ile Lys Cys Pro Leu Pro Glu Met His Val Arg Ile Tyr Leu
            35                  40                  45

Cys Arg Glu Met Ala Gly Ser Gly Thr Cys Gly Thr Val Val Ser Thr
        50                  55                  60

Thr Asn Phe Ile Lys Ala Glu Tyr Lys Gly Arg Val Thr Leu Lys Gln
 65                  70                  75                  80

Tyr Pro Arg Lys Asn Leu Phe Leu Val Glu Val Thr Gln Leu Thr Glu
                85                  90                  95

Ser Asp Ser Gly Val Tyr Ala Cys Gly Ala Gly Met Asn Thr Asp Arg
                100                 105                 110

Gly Lys Thr Gln Lys Val Thr Leu Asn Val His Ser Glu Tyr Glu Pro
            115                 120                 125

Ser Trp Glu Glu Gln Pro Met Pro Glu Thr Pro Lys Trp Phe His Leu
        130                 135                 140

Pro Tyr Leu Phe Gln Met Pro Ala Tyr Ala Ser Ser Lys Phe Val
145                 150                 155                 160

Thr Arg Val Thr Thr Pro Ala Gln Arg Gly Lys Val Pro Pro Val His
                165                 170                 175

His Ser Ser Pro Thr Thr Gln Ile Thr His Arg Pro Arg Val Ser Arg
            180                 185                 190

Ala Ser Ser Val Ala Gly Asp Lys Pro Arg Thr Phe Leu Pro Ser Thr
        195                 200                 205

Thr Ala Ser Lys Ile Ser Ala Leu Glu Gly Leu Leu Lys Pro Gln Thr
210                 215                 220

Pro Ser Tyr Asn His His Thr Arg Leu His Arg Gln Arg Ala Leu Asp
225                 230                 235                 240

Tyr Gly Ser Gln Ser Gly Arg Glu Gly Gln Gly Phe His Ile Leu Ile
                245                 250                 255

Pro Thr Ile Leu Gly Leu Phe Leu Leu Ala Leu Leu Gly Leu Val Val
            260                 265                 270

Lys Arg Ala Val Glu Arg Arg Lys Ala Leu Ser Arg Arg Ala Arg Arg
        275                 280                 285

Leu Ala Val Arg Met Arg Ala Leu Glu Ser Ser Gln Arg Pro Arg Gly
290                 295                 300

Ser Pro Arg Pro Arg Ser Gln Asn Asn Ile Tyr Ser Ala Cys Pro Arg
305                 310                 315                 320

Arg Ala Arg Gly Ala Asp Ala Ala Gly Thr Gly Glu Ala Pro Val Pro
                325                 330                 335

Gly Pro Gly Ala Pro Leu Pro Ala Pro Leu Gln Val Ser Glu Ser
            340                 345                 350

Pro Trp Leu His Ala Pro Ser Leu Lys Thr Ser Cys Glu Tyr Val Ser
        355                 360                 365

Leu Tyr His Gln Pro Ala Ala Met Met Glu Asp Ser Asp Ser Asp Asp
    370                 375                 380

Tyr Ile Asn Val Pro Ala
385                 390
```

<210> SEQ ID NO 3
<211> LENGTH: 84
<212> TYPE: PRT
<213> ORGANISM: Homo sapiens
<220> FEATURE:
<221> NAME/KEY: UNSURE
<222> LOCATION: (13)..(16)
<223> OTHER INFORMATION: The xaa at positions 13 through 16 represents
      an unknown amino acid.
<221> NAME/KEY: UNSURE
<222> LOCATION: (44)..(48)
<223> OTHER INFORMATION: The xaa at positions 44 through 48 represents
      an unknown amino acid.
<221> NAME/KEY: UNSURE
<222> LOCATION: (61)..(62)
<223> OTHER INFORMATION: The xaa at positions 61 and 62 represents an
      unknown amino acid.

<400> SEQUENCE: 3

Val Thr Ile Lys Cys Pro Leu Pro Glu Met His Val Xaa Xaa Xaa Xaa
 1               5                  10                  15

Arg Ile Tyr Lys Cys Arg Glu Asn Ala Gly Ser Gly Thr Cys Gly Thr
             20                  25                  30

Val Val Ser Thr Thr Asx Phe Ile Lys Ala Glu Xaa Xaa Xaa Xaa Xaa
         35                  40                  45

Tyr Lys Gly Arg Val Thr Leu Lys Gln Tyr Pro Arg Xaa Xaa Lys Asn
     50                  55                  60

Leu Phe Leu Val Glu Val Thr Glx Leu Thr Glu Ser Asp Ser Gly Val
 65                  70                  75                  80

Tyr Ala Cys Gly

<210> SEQ ID NO 4
<211> LENGTH: 84
<212> TYPE: PRT
<213> ORGANISM: Homo sapiens
<220> FEATURE:
<221> NAME/KEY: UNSURE
<222> LOCATION: (13)..(14)
<223> OTHER INFORMATION: The xaa at positions 13 and 14 represents an
      unknown amino acid.
<221> NAME/KEY: UNSURE
<222> LOCATION: (61)..(62)
<223> OTHER INFORMATION: The xaa at positions 61 and 62 represents an
      unknown amino acid.
<221> NAME/KEY: UNSURE
<222> LOCATION: (27)
<223> OTHER INFORMATION: The xaa at position 27 represents an unknown
      amino acid.

<400> SEQUENCE: 4

Leu Ser Leu Thr Cys Thr Val Ser Gly Ser Thr Phe Xaa Xaa Ser Asn
 1               5                  10                  15

Asp Tyr Tyr Thr Trp Val Arg Gln Pro Pro Xaa Gly Arg Gly Leu Glu
             20                  25                  30

Trp Ile Gly Tyr Val Phe Tyr His Gly Thr Ser Asp Asp Thr Thr Pro
         35                  40                  45

Leu Arg Ser Arg Val Thr Met Leu Val Asp Thr Ser Xaa Xaa Lys Asn
     50                  55                  60

Gln Phe Ser Leu Arg Leu Ser Ser Val Thr Ala Ala Asp Thr Ala Val
 65                  70                  75                  80

Tyr Tyr Cys Ala

<210> SEQ ID NO 5

```
<211> LENGTH: 84
<212> TYPE: PRT
<213> ORGANISM: Homo sapiens
<220> FEATURE:
<221> NAME/KEY: UNSURE
<222> LOCATION: (13)
<223> OTHER INFORMATION: The xaa at position 13 represents an unknown
      amino acid.
<221> NAME/KEY: UNSURE
<222> LOCATION: (45)..(50)
<223> OTHER INFORMATION: The xaa at positions 45 through 50 represents
      an unkown amino acid.
<221> NAME/KEY: UNSURE
<222> LOCATION: (60)..(63)
<223> OTHER INFORMATION: The xaa at positions 60 through 63 represents
      an unknown amino acid.

<400> SEQUENCE: 5

Val Thr Leu Thr Cys Arg Ser Ser Thr Gly Ala Val Xaa Thr Thr Ser
  1               5                  10                  15

Asn Tyr Ala Asn Trp Val Gln Gln Lys Pro Asp His Leu Phe Thr Gly
             20                  25                  30

Ile Gly Gly Thr Asn Asn Arg Ala Pro Gly Val Pro Xaa Xaa Xaa Xaa
         35                  40                  45

Xaa Xaa Ala Arg Phe Ser Gly Ser Leu Ile Gly Xaa Xaa Xaa Xaa Asn
     50                  55                  60

Lys Ala Ala Leu Thr Ile Thr Gly Ala Gln Thr Glu Asp Glu Ala Ile
 65                  70                  75                  80

Met Phe Cys Ala

<210> SEQ ID NO 6
<211> LENGTH: 84
<212> TYPE: PRT
<213> ORGANISM: Homo sapiens
<220> FEATURE:
<221> NAME/KEY: UNSURE
<222> LOCATION: (12)..(15)
<223> OTHER INFORMATION: The xaa at positions 12 through 15 represents
      an unknown amino acid.
<221> NAME/KEY: UNSURE
<222> LOCATION: (43)..(48)
<223> OTHER INFORMATION: The xaa at positions 43 through 48 represents
      an unknown amino acid.
<221> NAME/KEY: UNSURE
<222> LOCATION: (61)..(62)
<223> OTHER INFORMATION: The xaa at positions 61 through 62 represents
      an unknown amino acid.

<400> SEQUENCE: 6

Thr Ser Leu Asn Cys Thr Phe Ser Asp Ser Ala Xaa Xaa Xaa Xaa Ser
  1               5                  10                  15

Gln Tyr Phe Trp Trp Tyr Arg Gln His Ser Gly Lys Ala Pro Lys Ala
             20                  25                  30

Leu Met Ser Ile Phe Ser Asn Gly Glu Lys Xaa Xaa Xaa Xaa Xaa Xaa
         35                  40                  45

Glu Glu Gly Arg Phe Thr Ile His Leu Asn Lys Ala Xaa Xaa Ser Leu
     50                  55                  60

His Phe Ser Leu His Ile Arg Asp Ser Gln Pro Ser Asp Ser Ala Leu
 65                  70                  75                  80

Tyr Leu Cys Ala

<210> SEQ ID NO 7
<211> LENGTH: 84
<212> TYPE: PRT
<213> ORGANISM: Homo sapiens
```

```
<220> FEATURE:
<221> NAME/KEY: UNSURE
<222> LOCATION: (11)..(14)
<223> OTHER INFORMATION: The xaa at positions 11 through 14 represents
      an unknown amino acid.
<221> NAME/KEY: UNSURE
<222> LOCATION: (18)
<223> OTHER INFORMATION: The xaa at position 18 represents an unknown
      amino acid.
<221> NAME/KEY: UNSURE
<222> LOCATION: (28)
<223> OTHER INFORMATION: The xaa at position 28 represents an unknown
      amino acid.
<221> NAME/KEY: UNSURE
<222> LOCATION: (59)..(61)
<223> OTHER INFORMATION: The xaa at positions 59 through 61 represents
      an unknown amino acid.

<400> SEQUENCE: 7

Val Thr Leu Arg Cys Lys Pro Ile Ser Gly Xaa Xaa Xaa Xaa His Asn
 1               5                  10                  15

Ser Xaa Leu Phe Trp Tyr Arg Gln Thr Met Met Xaa Arg Gly Leu Glu
            20                  25                  30

Leu Leu Ile Tyr Phe Asn Asn Asn Val Pro Ile Asp Asp Ser Gly Met
        35                  40                  45

Pro Glu Asp Arg Phe Ser Ala Lys Met Pro Xaa Xaa Xaa Asn Ala Ser
    50                  55                  60

Phe Ser Thr Leu Lys Ile Gln Pro Ser Glu Pro Arg Asp Ser Ala Val
65                  70                  75                  80

Tyr Phe Cys Ala

<210> SEQ ID NO 8
<211> LENGTH: 84
<212> TYPE: PRT
<213> ORGANISM: Homo sapiens
<220> FEATURE:
<221> NAME/KEY: UNSURE
<222> LOCATION: (11)..(14)
<223> OTHER INFORMATION: The xaa at positions 11 through 14 represents
      an unknown amino acid.
<221> NAME/KEY: UNSURE
<222> LOCATION: (28)
<223> OTHER INFORMATION: The xaa at position 28 represents an unknown
      amino acid.
<221> NAME/KEY: UNSURE
<222> LOCATION: (41)
<223> OTHER INFORMATION: The xaa at position 41 represents an unknown
      amino acid.
<221> NAME/KEY: UNSURE
<222> LOCATION: (46)..(48)
<223> OTHER INFORMATION: The xaa at positions 46 through 48 represents
      an unknown amino acid.
<221> NAME/KEY: UNSURE
<222> LOCATION: (62)
<223> OTHER INFORMATION: The xaa at position 62 represents an unknown
      amino acid.

<400> SEQUENCE: 8

Val Glu Leu Thr Cys Thr Ala Ser Gln Lys Xaa Xaa Xaa Xaa Lys Ser
 1               5                  10                  15

Ile Gln Phe His Trp Lys Asn Ser Asn Gln Ile Xaa Lys Ile Leu Gly
            20                  25                  30

Asn Gln Gly Ser Phe Leu Thr Lys Xaa Gly Pro Ser Lys Xaa Xaa Xaa
        35                  40                  45

Leu Asn Asp Arg Ala Asp Ser Arg Arg Ser Leu Trp Asp Xaa Gln Gly
    50                  55                  60

Asn Phe Pro Leu Ile Ile Lys Asn Leu Lys Ile Glu Asp Ser Asp Thr
```

```
                65                  70                  75                  80

Tyr Ile Cys Glu

<210> SEQ ID NO 9
<211> LENGTH: 84
<212> TYPE: PRT
<213> ORGANISM: Homo sapiens
<220> FEATURE:
<221> NAME/KEY: UNSURE
<222> LOCATION: (12)..(14)
<223> OTHER INFORMATION: The xaa at positions 12 through 14 represents
      an unknown amino acid.
<221> NAME/KEY: UNSURE
<222> LOCATION: (41)
<223> OTHER INFORMATION: The xaa at position 41 represents an unknown
      amino acid.

<400> SEQUENCE: 9

Ala Lys Met Ser Cys Glu Ala Lys Thr Phe Pro Xaa Xaa Xaa Lys Gly
  1               5                  10                  15

Thr Thr Ile Tyr Trp Leu Arg Glu Leu Gln Asp Ser Asn Lys Asn Lys
                 20                  25                  30

His Phe Glu Phe Leu Ala Ser Arg Xaa Thr Ser Thr Lys Gly Ile Lys
             35                  40                  45

Tyr Gly Glu Arg Val Lys Lys Asn Met Thr Leu Ser Phe Asn Ser Thr
 50                  55                  60

Leu Pro Phe Leu Lys Ile Met Asp Val Lys Pro Glu Asp Ser Gly Phe
 65                  70                  75                  80

Tyr Phe Cys Ala

<210> SEQ ID NO 10
<211> LENGTH: 84
<212> TYPE: PRT
<213> ORGANISM: Homo sapiens
<220> FEATURE:
<221> NAME/KEY: UNSURE
<222> LOCATION: (13)..(14)
<223> OTHER INFORMATION: The xaa at positions 13 and 14 represents an
      unkown amino acid.
<221> NAME/KEY: UNSURE
<222> LOCATION: (26)..(30)
<223> OTHER INFORMATION: The xaa at positions 26 through 30 represents
      an unknown amino acid.
<221> NAME/KEY: UNSURE
<222> LOCATION: (61)
<223> OTHER INFORMATION: The xaa at position 61 represents an unknown
      amino acid.

<400> SEQUENCE: 10

Val Thr Ile Thr Cys Pro Phe Thr Tyr Ala Thr Arg Xaa Xaa Gln Leu
  1               5                  10                  15

Lys Lys Ser Phe Tyr Lys Val Glu Asp Xaa Xaa Xaa Xaa Xaa Gly Glu
                 20                  25                  30

Leu Val Leu Ile Ile Asp Ser Ser Lys Glu Ala Lys Asp Pro Arg
             35                  40                  45

Tyr Lys Gly Arg Ile Thr Leu Gln Ile Gln Ser Thr Xaa Thr Ala Lys
 50                  55                  60

Glu Phe Thr Val Thr Leu Lys His Leu Gln Leu Asn Asp Ala Gly Gln
 65                  70                  75                  80

Tyr Val Cys Gln

<210> SEQ ID NO 11
<211> LENGTH: 84
```

```
<212> TYPE: PRT
<213> ORGANISM: Unknown
<220> FEATURE:
<221> NAME/KEY: UNSURE
<222> LOCATION: (53)
<223> OTHER INFORMATION: The x at position 53 can represent either
      Phenylalanine, Valine or Isoleucine.
<221> NAME/KEY: UNSURE
<222> LOCATION: (79)
<223> OTHER INFORMATION: The x at position 79 can represent either
      Alanine or Glycine.
<223> OTHER INFORMATION: Description of Unknown Organism: Consensus
<221> NAME/KEY: UNSURE
<222> LOCATION: (6)..(18)
<223> OTHER INFORMATION: The xaa at positions 6 through 18 represents an
      unknown amino acid.
<221> NAME/KEY: UNSURE
<222> LOCATION: (20)
<223> OTHER INFORMATION: The xaa at position 20 represents an unknown
      amino acid.
<221> NAME/KEY: UNSURE
<222> LOCATION: (22)
<223> OTHER INFORMATION: The xaa at position 22 represents an unknown
      amino acid.
<221> NAME/KEY: UNSURE
<222> LOCATION: (25)..(32)
<223> OTHER INFORMATION: The xaa at positions 25 through 32 represents
      an unknown amino acid.
<221> NAME/KEY: UNSURE
<222> LOCATION: (34)..(35)
<223> OTHER INFORMATION: The xaa at positions 34 and 35 represents an
      unknown amino acid.
<221> NAME/KEY: UNSURE
<222> LOCATION: (37)..(48)
<223> OTHER INFORMATION: The xaa at positions 37 through 48 represents
      an unknown amino acid.
<221> NAME/KEY: UNSURE
<222> LOCATION: (50)..(51)
<223> OTHER INFORMATION: The xaa at positions 50 and 51 represents an
      unknown amino acid.
<221> NAME/KEY: UNSURE
<222> LOCATION: (54)..(65)
<223> OTHER INFORMATION: The xaa at positions 54 through 65 represents
      an unknown amino acid.
<221> NAME/KEY: UNSURE
<222> LOCATION: (71)
<223> OTHER INFORMATION: The xaa at position 71 represents an unknown
      amino acid.
<221> NAME/KEY: UNSURE
<222> LOCATION: (73)..(76)
<223> OTHER INFORMATION: The xaa at positions 73 through 76 represents
      an unknown amino acid.
<221> NAME/KEY: UNSURE
<222> LOCATION: (80)
<223> OTHER INFORMATION: The xaa at position 80 represents an unknown
      amino acid.
<221> NAME/KEY: UNSURE
<222> LOCATION: (82)
<223> OTHER INFORMATION: The xaa at position 82 represents an unknown
      amino acid.

<400> SEQUENCE: 11

Val Thr Leu Thr Cys Xaa Xaa Ser Xaa Xaa Xaa Xaa Xaa Xaa Xaa
 1               5                  10                  15

Xaa Xaa Phe Xaa Trp Xaa Arg Gln Xaa Xaa Xaa Xaa Xaa Xaa Xaa
             20                  25                  30

Leu Xaa Xaa Tyr Xaa Xaa Xaa Xaa Xaa Xaa Xaa Xaa Xaa Xaa Xaa
         35                  40                  45

Tyr Xaa Xaa Arg Xaa Xaa Xaa Xaa Xaa Xaa Xaa Xaa Xaa Xaa Xaa
     50                  55                  60

Xaa Phe Ser Leu Thr Ile Xaa Asn Xaa Xaa Xaa Asp Ser Xaa Xaa
 65                  70                  75                  80

Tyr Xaa Cys Ala
```

<210> SEQ ID NO 12
<211> LENGTH: 43
<212> TYPE: PRT
<213> ORGANISM: Homo sapiens

<400> SEQUENCE: 12

Gln Arg Pro Arg Gly Ser Pro Arg Pro Arg Ser Gln Asn Asn Ile Tyr
 1               5                  10                  15

Ser Ala Cys Pro Arg Arg Ala Arg Gly Ala Asp Ala Ala Gly Thr Gly
                20                  25                  30

Glu Ala Pro Val Pro Gly Pro Gly Ala Pro Leu
            35                  40

<210> SEQ ID NO 13
<211> LENGTH: 43
<212> TYPE: PRT
<213> ORGANISM: Homo sapiens
<220> FEATURE:
<221> NAME/KEY: UNSURE
<222> LOCATION: (12)..(19)
<223> OTHER INFORMATION: The xaa at positions 12 through 19 represents
      an unknown amino acid.

<400> SEQUENCE: 13

Arg Arg Pro Arg Gly Glu Pro Gly Pro Arg Ala Xaa Xaa Xaa Xaa Xaa
 1               5                  10                  15

Xaa Xaa Xaa Pro Arg Pro Thr Glu Gly Ala Thr Cys Ala Gly Pro Gly
                20                  25                  30

Glu Ser Trp Ser Pro Ser Pro Asn Ser Met Leu
            35                  40

<210> SEQ ID NO 14
<211> LENGTH: 36
<212> TYPE: PRT
<213> ORGANISM: Homo sapiens

<400> SEQUENCE: 14

Met Pro Pro Arg Tyr Gly Ser Leu Arg Gln Ser Cys Pro Arg Ser Gly
 1               5                  10                  15

Arg Glu Gln Gly Gln Asp Gly Thr Ala Gly Ala Pro Gly Leu Leu Trp
                20                  25                  30

Met Gly Leu Val
            35

<210> SEQ ID NO 15
<211> LENGTH: 19
<212> TYPE: PRT
<213> ORGANISM: Homo sapiens

<400> SEQUENCE: 15

Glu Ser Pro Trp Leu His Ala Pro Ser Leu Lys Thr Ser Cys Glu Tyr
 1               5                  10                  15

Val Ser Leu

<210> SEQ ID NO 16
<211> LENGTH: 19
<212> TYPE: PRT
<213> ORGANISM: Homo sapiens

<400> SEQUENCE: 16

Asp Ala Pro Trp Gln Gln His Ala Arg Trp Tyr Asp Arg Cys Glu Tyr

```
                1               5                  10                 15
Val Leu Leu

<210> SEQ ID NO 17
<211> LENGTH: 19
<212> TYPE: PRT
<213> ORGANISM: Homo sapiens

<400> SEQUENCE: 17

Gln Gln Pro Leu Leu His Pro Pro Glu Pro Lys Ser Pro Gly Glu Tyr
  1               5                  10                 15

Val Asn Ile

<210> SEQ ID NO 18
<211> LENGTH: 19
<212> TYPE: PRT
<213> ORGANISM: Homo sapiens

<400> SEQUENCE: 18

Trp Glu Pro Trp Leu Pro Ala Glu Ala Leu Thr Arg Leu Arg Ile Gly
  1               5                  10                 15

Gly Phe Tyr

<210> SEQ ID NO 19
<211> LENGTH: 19
<212> TYPE: PRT
<213> ORGANISM: Homo sapiens

<400> SEQUENCE: 19

Gln Pro Ala Ala Met Met Glu Asp Ser Asp Ser Asp Asp Tyr Ile Asn
  1               5                  10                 15

Val Pro Ala

<210> SEQ ID NO 20
<211> LENGTH: 19
<212> TYPE: PRT
<213> ORGANISM: Homo sapiens

<400> SEQUENCE: 20

Thr Glu Ala Cys Val Val Arg Asp Ala Asp Asn Glu Pro His Ile Glu
  1               5                  10                 15

Arg Pro Ala

<210> SEQ ID NO 21
<211> LENGTH: 19
<212> TYPE: PRT
<213> ORGANISM: Homo sapiens

<400> SEQUENCE: 21

Gln Pro Ala Pro Arg Glu Glu Glu Thr Gly Thr Glu Glu Tyr Met Lys
  1               5                  10                 15

Met Asp Leu

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 22
```
gctcacttac aggctctcta                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
caggtggggt ctttcattcc                                              20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 24
agaggcatag ctattgtctc gg                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
acatttggat cagggcaaag                                              20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 26
aggggctctt ggatggac                                                18

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 27
ctggggttgg ggatagc                                                 17

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 28
gggagaagta aagaacaaag                                              20

<210> SEQ ID NO 29
<211> LENGTH: 20
<212> TYPE: DNA
<213> ORGANISM: Artificial Sequence

```
<220> FEATURE:
<223> OTHER INFORMATION: Description of Artificial Sequence: Synthetic

<400> SEQUENCE: 29
cgtaggcaca atcacagcat                                              20

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 30
agaattctct ctagggctc ttggatg                                       27

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 31
ataaagcttc tcagggcaca gatagatgg                                    29
```